United States Patent
Lin et al.

(10) Patent No.: US 11,439,419 B2
(45) Date of Patent: Sep. 13, 2022

(54) ADVANCED BASKET DRIVE MODE

(71) Applicant: AURIS HEALTH, INC., Redwood City, CA (US)

(72) Inventors: Jiayi Lin, San Mateo, CA (US); Chauncey F. Graetzel, Palo Alto, CA (US); Sarah Plewe, Redwood City, CA (US); Rachel Leigh Chok, Sunnyvale, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 17/121,167

(22) Filed: Dec. 14, 2020

(65) Prior Publication Data

US 2021/0196293 A1    Jul. 1, 2021

Related U.S. Application Data

(60) Provisional application No. 62/956,071, filed on Dec. 31, 2019.

(51) Int. Cl.
*A61B 17/221* (2006.01)
*A61B 34/00* (2016.01)
(Continued)

(52) U.S. Cl.
CPC ........ *A61B 17/221* (2013.01); *A61B 1/00006* (2013.01); *A61B 1/00149* (2013.01);
(Continued)

(58) Field of Classification Search
CPC .................................................... A61B 17/221
See application file for complete search history.

(56) References Cited

U.S. PATENT DOCUMENTS

| 2,556,601 A | 6/1951 | Schofield |
|---|---|---|
| 2,566,183 A | 8/1951 | Forss |

(Continued)

FOREIGN PATENT DOCUMENTS

| AU | 2017336790 A1 | 4/2019 |
|---|---|---|
| AU | 2018243364 A1 | 10/2019 |

(Continued)

OTHER PUBLICATIONS

International search report for PCT/IB2020/061905, dated Mar. 18, 2021, 8 pages.

(Continued)

*Primary Examiner* — Scott Luan
(74) *Attorney, Agent, or Firm* — Chang & Hale LLP

(57) ABSTRACT

A robotic system includes a robotic manipulator configured to: manipulate a medical instrument having a basket; open the basket at a first opening speed and a second, faster opening speed; and close the basket at a first closing speed and a second, faster closing speed. The system includes an input device configured to receive one or more user interactions and initiate one or more actions by the robotic manipulator, including directly controlled movement and/or pre-programmed motions. Control circuitry of the robotic system is configured to: in response to receiving a first user interaction via the input device, trigger a first pre-programmed motion of the robotic manipulator to open the basket at the second, faster opening speed; and in response to receiving a second user interaction via the input device, trigger a second pre-programmed motion to close the basket at the second, faster closing speed.

30 Claims, 11 Drawing Sheets

(51) Int. Cl.
  *A61B 34/30* (2016.01)
  *A61B 1/00* (2006.01)
  *A61B 1/307* (2006.01)
  *A61B 90/00* (2016.01)
(52) U.S. Cl.
  CPC .............. *A61B 1/307* (2013.01); *A61B 34/30* (2016.02); *A61B 34/74* (2016.02); *A61B 2034/301* (2016.02); *A61B 2034/742* (2016.02); *A61B 2034/743* (2016.02); *A61B 2034/744* (2016.02); *A61B 2090/066* (2016.02)

(56) References Cited

U.S. PATENT DOCUMENTS

| | | |
|---|---|---|
| 2,623,175 A | 12/1952 | Finke |
| 2,730,699 A | 1/1956 | Gratian |
| 2,884,808 A | 5/1959 | Mueller |
| 3,294,183 A | 12/1966 | Riley et al. |
| 3,472,083 A | 10/1969 | Schnepel |
| 3,513,724 A | 5/1970 | Box |
| 3,595,074 A | 7/1971 | Johnson |
| 3,734,207 A | 5/1973 | Fishbein |
| 3,739,923 A | 6/1973 | Totsuka |
| 3,763,860 A | 10/1973 | Clarke |
| 3,784,031 A | 1/1974 | Niitu et al. |
| 3,790,002 A | 2/1974 | Guilbaud et al. |
| 3,921,536 A | 11/1975 | Savage |
| 3,926,386 A | 12/1975 | Stahmann et al. |
| 4,040,413 A | 8/1977 | Ohshiro |
| 4,141,245 A | 2/1979 | Brandstetter |
| 4,198,960 A | 4/1980 | Utsugi |
| 4,241,884 A | 12/1980 | Lynch |
| 4,243,034 A | 1/1981 | Brandt |
| 4,351,493 A | 9/1982 | Sonnek |
| 4,357,843 A | 11/1982 | Peck et al. |
| 4,384,493 A | 5/1983 | Grunbaum |
| 4,470,407 A | 9/1984 | Hussein |
| 4,507,026 A | 3/1985 | Lund |
| 4,530,471 A | 7/1985 | Inoue |
| 4,532,935 A | 8/1985 | Wang |
| 4,555,960 A | 12/1985 | King |
| 4,611,594 A | 9/1986 | Grayhack et al. |
| 4,685,458 A | 8/1987 | Leckrone |
| 4,688,555 A | 8/1987 | Wardle |
| 4,741,335 A | 5/1988 | Okada |
| 4,745,908 A | 5/1988 | Wardle |
| 4,747,405 A | 5/1988 | Leckrone |
| 4,784,150 A | 11/1988 | Voorhies et al. |
| 4,854,301 A | 8/1989 | Nakajima |
| 4,857,058 A | 8/1989 | W. |
| 4,898,574 A | 2/1990 | Uchiyama et al. |
| 4,899,733 A | 2/1990 | DeCastro et al. |
| 4,907,168 A | 3/1990 | Boggs |
| 4,945,790 A | 8/1990 | Golden |
| 4,983,165 A | 1/1991 | Loiterman |
| 5,029,574 A | 7/1991 | Shimamura et al. |
| 5,085,659 A | 2/1992 | Rydell |
| 5,150,452 A | 9/1992 | Pollack et al. |
| 5,190,542 A | 3/1993 | Nakao et al. |
| 5,190,557 A | 3/1993 | Borodulin et al. |
| 5,196,023 A | 3/1993 | Martin |
| 5,207,128 A | 5/1993 | Albright |
| 5,217,465 A | 6/1993 | Steppe |
| 5,234,428 A | 8/1993 | Kaufman |
| 5,256,150 A | 10/1993 | Quiachon et al. |
| 5,277,085 A | 1/1994 | Tanimura et al. |
| 5,308,323 A | 5/1994 | Sogawa et al. |
| 5,318,589 A | 6/1994 | Lichtman |
| 5,325,848 A | 7/1994 | Adams et al. |
| 5,342,381 A | 8/1994 | Tidemand |
| 5,344,395 A | 9/1994 | Whalen et al. |
| 5,350,101 A | 9/1994 | Godlewski |
| 5,353,783 A | 10/1994 | Nakao et al. |
| 5,370,609 A | 12/1994 | Drasler et al. |
| 5,372,124 A | 12/1994 | Takayama et al. |
| 5,411,016 A | 5/1995 | Kume et al. |
| 5,426,687 A | 6/1995 | Goodall et al. |
| 5,431,649 A | 7/1995 | Mulier et al. |
| 5,441,485 A | 8/1995 | Peters |
| 5,449,356 A | 9/1995 | Walbrink et al. |
| 5,450,843 A | 9/1995 | Moll et al. |
| 5,472,426 A | 12/1995 | Bonati et al. |
| 5,496,267 A | 3/1996 | Drasler et al. |
| 5,501,667 A | 3/1996 | Verduin, Jr. |
| 5,507,725 A | 4/1996 | Savage et al. |
| 5,520,684 A | 5/1996 | Imran |
| 5,524,180 A | 6/1996 | Wang et al. |
| 5,545,170 A | 8/1996 | Hart |
| 5,559,294 A | 9/1996 | Hoium et al. |
| 5,562,239 A | 10/1996 | Boiarski et al. |
| 5,562,648 A | 10/1996 | Peterson |
| 5,562,678 A | 10/1996 | Booker |
| 5,572,999 A | 11/1996 | Funda et al. |
| 5,573,535 A | 11/1996 | Viklund |
| 5,613,973 A | 3/1997 | Jackson et al. |
| 5,645,083 A | 7/1997 | Essig et al. |
| 5,653,374 A | 8/1997 | Young et al. |
| 5,658,311 A | 8/1997 | Baden |
| 5,695,500 A | 12/1997 | Taylor et al. |
| 5,697,949 A | 12/1997 | Giurtino et al. |
| 5,709,661 A | 1/1998 | Egmond et al. |
| 5,710,870 A | 1/1998 | Ohm et al. |
| 5,716,325 A | 2/1998 | Bonutti |
| 5,737,500 A | 4/1998 | Seraji et al. |
| 5,767,840 A | 6/1998 | Selker |
| 5,779,623 A | 7/1998 | Bonnell |
| 5,788,667 A | 8/1998 | Stoller |
| 5,788,710 A | 8/1998 | Bates et al. |
| 5,792,135 A | 8/1998 | Madhani et al. |
| 5,792,165 A | 8/1998 | Klieman et al. |
| 5,797,900 A | 8/1998 | Madhani et al. |
| 5,798,627 A | 8/1998 | Gilliland et al. |
| 5,810,770 A | 9/1998 | Chin et al. |
| 5,842,390 A | 12/1998 | Bouligny et al. |
| 5,855,583 A | 1/1999 | Wang et al. |
| 5,893,869 A | 4/1999 | Barnhart et al. |
| 5,897,491 A | 4/1999 | Kastenbauer et al. |
| 5,921,968 A | 7/1999 | Lampropoulos et al. |
| 5,924,175 A | 7/1999 | Lippitt et al. |
| 5,943,056 A | 8/1999 | Sato et al. |
| 5,967,934 A | 10/1999 | Ishida et al. |
| 5,969,230 A | 10/1999 | Sakai et al. |
| 5,989,230 A | 11/1999 | Frassica |
| 6,071,281 A | 6/2000 | Burnside et al. |
| 6,077,219 A | 6/2000 | Viebach et al. |
| 6,084,371 A | 7/2000 | Kress et al. |
| 6,093,157 A | 7/2000 | Chandrasekaran |
| 6,110,171 A | 8/2000 | Rydell |
| 6,120,476 A | 9/2000 | Fung et al. |
| 6,120,498 A | 9/2000 | Jani et al. |
| 6,154,000 A | 11/2000 | Rastegar et al. |
| 6,156,030 A | 12/2000 | Neev |
| 6,159,220 A | 12/2000 | Gobron et al. |
| 6,171,234 B1 | 1/2001 | White et al. |
| 6,174,318 B1 | 1/2001 | Bates et al. |
| 6,183,435 B1 | 2/2001 | Bumbalough et al. |
| 6,183,482 B1 | 2/2001 | Bates et al. |
| 6,185,478 B1 | 2/2001 | Koakutsu et al. |
| 6,206,903 B1 | 3/2001 | Ramans |
| 6,236,906 B1 | 5/2001 | Müller |
| 6,272,371 B1 | 8/2001 | Shlomo |
| 6,289,579 B1 | 9/2001 | Viza et al. |
| 6,302,895 B1 | 10/2001 | Gobron et al. |
| 6,322,557 B1 | 11/2001 | Nikolaevich et al. |
| 6,375,635 B1 | 4/2002 | Moutafis et al. |
| 6,394,998 B1 | 5/2002 | Wallace et al. |
| 6,401,572 B1 | 6/2002 | Provost |
| 6,405,078 B1 | 6/2002 | Moaddeb et al. |
| 6,428,563 B1 | 8/2002 | Keller |
| 6,436,107 B1 | 8/2002 | Wang et al. |
| 6,440,061 B1 | 8/2002 | Wenner et al. |
| 6,487,940 B2 | 12/2002 | Hart et al. |
| 6,491,701 B2 | 12/2002 | Tierney et al. |
| 6,508,823 B1 | 1/2003 | Gonon |

(56) References Cited

U.S. PATENT DOCUMENTS

| | | |
|---|---|---|
| 6,522,906 B1 | 2/2003 | Salisbury et al. |
| 6,577,891 B1 | 6/2003 | Jaross et al. |
| 6,659,939 B2 | 12/2003 | Moll et al. |
| 6,673,080 B2 | 1/2004 | Reynolds et al. |
| 6,676,668 B2 | 1/2004 | Mercereau et al. |
| 6,685,698 B2 | 2/2004 | Morley et al. |
| 6,695,818 B2 | 2/2004 | Wollschläger |
| 6,706,050 B1 | 3/2004 | Giannadakis |
| 6,726,675 B1 | 4/2004 | Beyar |
| 6,786,896 B1 | 9/2004 | Madhani et al. |
| 6,827,712 B2 | 12/2004 | Tovey et al. |
| 6,991,602 B2 | 1/2006 | Nakazawa et al. |
| 7,044,936 B2 | 5/2006 | Harding et al. |
| 7,172,580 B2 | 2/2007 | Hruska et al. |
| 7,248,944 B2 | 7/2007 | Green |
| 7,276,044 B2 | 10/2007 | Ferry et al. |
| 7,282,055 B2 | 10/2007 | Tsuruta |
| 7,524,284 B2 | 4/2009 | Murakami et al. |
| 7,559,934 B2 | 7/2009 | Teague et al. |
| 7,615,042 B2 | 11/2009 | Beyar et al. |
| 7,635,342 B2 | 12/2009 | Ferry et al. |
| 7,645,283 B2 | 1/2010 | Reynolds et al. |
| 7,736,356 B2 | 6/2010 | Cooper et al. |
| 7,766,856 B2 | 8/2010 | Ferry et al. |
| 7,882,841 B2 | 2/2011 | Aljuri et al. |
| 7,914,540 B2 | 3/2011 | Schwartz et al. |
| 7,938,809 B2 | 5/2011 | Lampropoulos et al. |
| 7,963,911 B2 | 6/2011 | Turliuc |
| 7,972,298 B2 | 7/2011 | Wallace et al. |
| 7,974,674 B2 | 7/2011 | Hauck et al. |
| 7,987,046 B1 | 7/2011 | Peterman et al. |
| 7,998,020 B2 | 8/2011 | Kidd et al. |
| 8,002,713 B2 | 8/2011 | Heske et al. |
| 8,004,229 B2 | 8/2011 | Nowlin et al. |
| 8,016,839 B2 | 9/2011 | Wilk |
| 8,038,598 B2 | 10/2011 | Khachi |
| 8,043,303 B2 | 10/2011 | Razvi et al. |
| 8,052,636 B2 | 11/2011 | Moll et al. |
| 8,092,397 B2 | 1/2012 | Wallace et al. |
| 8,157,308 B2 | 4/2012 | Pedersen |
| 8,182,415 B2 | 5/2012 | Larkin et al. |
| 8,187,173 B2 | 5/2012 | Miyoshi |
| 8,257,303 B2 | 9/2012 | Moll et al. |
| 8,277,417 B2 | 10/2012 | Fedinec |
| 8,291,791 B2 | 10/2012 | Light et al. |
| 8,414,505 B1 | 4/2013 | Weitzner et al. |
| 8,425,465 B2 | 4/2013 | Nagano et al. |
| 8,480,595 B2 | 7/2013 | Speeg et al. |
| 8,523,762 B2 | 9/2013 | Miyamoto et al. |
| 8,540,748 B2 | 9/2013 | Murphy et al. |
| 8,541,970 B2 | 9/2013 | Nowlin et al. |
| 8,602,031 B2 | 12/2013 | Reis et al. |
| 8,671,817 B1 | 3/2014 | Bogusky |
| 8,720,448 B2 | 5/2014 | Reis et al. |
| 8,746,252 B2 | 6/2014 | McGrogan et al. |
| 8,749,190 B2 | 6/2014 | Nowlin et al. |
| 8,755,124 B2 | 6/2014 | Aschwanden et al. |
| 8,786,241 B2 | 7/2014 | Nowlin et al. |
| 8,820,603 B2 | 9/2014 | Shelton, IV et al. |
| 8,821,480 B2 | 9/2014 | Burbank |
| 8,827,948 B2 | 9/2014 | Romo et al. |
| 8,870,815 B2 | 10/2014 | Bhat et al. |
| 8,882,660 B2 | 11/2014 | Phee et al. |
| 8,894,610 B2 | 11/2014 | MacNamara et al. |
| 8,945,163 B2 | 2/2015 | Voegele et al. |
| 8,956,280 B2 | 2/2015 | Eversull et al. |
| 8,961,533 B2 | 2/2015 | Stahler et al. |
| 8,968,333 B2 | 3/2015 | Yu et al. |
| 8,992,542 B2 | 3/2015 | Hagag et al. |
| 9,173,713 B2 | 11/2015 | Hart et al. |
| 9,179,979 B2 | 11/2015 | Jinno |
| 9,204,933 B2 | 12/2015 | Reis et al. |
| 9,254,123 B2 | 2/2016 | Alvarez et al. |
| 9,259,280 B2 | 2/2016 | Au et al. |
| 9,259,281 B2 | 2/2016 | Griffiths et al. |
| 9,259,282 B2 | 2/2016 | Azizian et al. |
| 9,296,104 B2 | 3/2016 | Swarup et al. |
| 9,326,822 B2 | 5/2016 | Lewis et al. |
| 9,345,456 B2 | 5/2016 | Tsonton et al. |
| 9,345,544 B2 | 5/2016 | Hourtash et al. |
| 9,375,284 B2 | 6/2016 | Hourtash |
| 9,408,669 B2 | 8/2016 | Kokish et al. |
| 9,415,510 B2 | 8/2016 | Hourtash et al. |
| 9,446,177 B2 | 9/2016 | Millman et al. |
| 9,452,018 B2 | 9/2016 | Yu |
| 9,457,168 B2 | 10/2016 | Moll et al. |
| 9,460,536 B2 | 10/2016 | Hasegawa et al. |
| 9,480,534 B2 | 11/2016 | Bowling et al. |
| 9,498,601 B2 | 11/2016 | Tanner et al. |
| 9,504,604 B2 | 11/2016 | Alvarez |
| 9,510,911 B2 | 12/2016 | Hourtash |
| 9,517,106 B2 | 12/2016 | Hourtash et al. |
| 9,561,083 B2 | 2/2017 | Yu et al. |
| 9,566,125 B2 | 2/2017 | Bowling et al. |
| 9,592,042 B2 | 3/2017 | Titus |
| 9,597,152 B2 | 3/2017 | Schaeffer et al. |
| 9,622,827 B2 | 4/2017 | Yu et al. |
| 9,636,184 B2 | 5/2017 | Lee et al. |
| 9,636,483 B2 | 5/2017 | Hart et al. |
| 9,668,814 B2 | 6/2017 | Kokish |
| 9,675,422 B2 | 6/2017 | Hourtash et al. |
| 9,687,310 B2 | 6/2017 | Nowlin et al. |
| 9,713,509 B2 | 7/2017 | Schuh et al. |
| 9,727,963 B2 | 8/2017 | Mintz et al. |
| 9,730,757 B2 | 8/2017 | Brudniok |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,818,681 B2 | 11/2017 | Machida |
| 9,844,412 B2 | 12/2017 | Bogusky et al. |
| 9,867,635 B2 | 1/2018 | Alvarez et al. |
| 9,918,659 B2 | 3/2018 | Chopra et al. |
| 9,918,681 B2 | 3/2018 | Wallace et al. |
| 9,931,025 B1 | 4/2018 | Graetzel et al. |
| 9,943,962 B2 | 4/2018 | Sattler et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |
| 9,993,313 B2 | 6/2018 | Schuh et al. |
| 9,993,614 B2 | 6/2018 | Pacheco et al. |
| 10,016,900 B1 | 7/2018 | Meyer et al. |
| 10,022,192 B1 | 7/2018 | Ummalaneni |
| 10,029,367 B2 | 7/2018 | Hourtash |
| 10,046,140 B2 | 8/2018 | Kokish et al. |
| 10,071,479 B2 | 9/2018 | Swarup et al. |
| 10,080,576 B2 | 9/2018 | Romo et al. |
| 10,117,713 B2 | 11/2018 | Barrera et al. |
| 10,130,429 B1 | 11/2018 | Weir |
| 10,136,949 B2 | 11/2018 | Felder et al. |
| 10,136,959 B2 | 11/2018 | Mintz et al. |
| 10,143,360 B2 | 12/2018 | Roelle et al. |
| 10,145,747 B1 | 12/2018 | Lin et al. |
| 10,149,720 B2 | 12/2018 | Romo |
| 10,154,822 B2 | 12/2018 | Henderson et al. |
| 10,159,532 B1 | 12/2018 | Ummalaneni |
| 10,159,533 B2 | 12/2018 | Moll et al. |
| 10,169,875 B2 | 1/2019 | Mintz et al. |
| 10,176,681 B2 | 1/2019 | Plewe et al. |
| 10,213,264 B2 | 2/2019 | Tanner et al. |
| 10,219,867 B2 | 3/2019 | Saglam et al. |
| 10,219,868 B2 | 3/2019 | Weir |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,258,285 B2 | 4/2019 | Hauck et al. |
| 10,285,574 B2 | 5/2019 | Landey et al. |
| 10,299,870 B2 | 5/2019 | Connolly et al. |
| 10,314,463 B2 | 6/2019 | Agrawal et al. |
| 10,314,661 B2 | 6/2019 | Bowling et al. |
| 10,327,855 B2 | 6/2019 | Hourtash et al. |

(56) References Cited

U.S. PATENT DOCUMENTS

| | | |
|---|---|---|
| 10,350,017 B2 | 7/2019 | Bowling et al. |
| 10,350,390 B2 | 7/2019 | Moll et al. |
| 10,363,103 B2 | 7/2019 | Alvarez et al. |
| 10,383,765 B2 | 8/2019 | Alvarez et al. |
| 10,398,518 B2 | 9/2019 | Yu et al. |
| 10,405,939 B2 | 9/2019 | Romo |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer et al. |
| 10,454,347 B2 | 10/2019 | Covington et al. |
| 10,463,440 B2 | 11/2019 | Bowling et al. |
| 10,464,209 B2 | 11/2019 | Ho et al. |
| 10,470,830 B2 | 11/2019 | Hill et al. |
| 10,478,595 B2 | 11/2019 | Kokish |
| 10,482,599 B2 | 11/2019 | Mintz et al. |
| 10,493,239 B2 | 12/2019 | Hart et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan et al. |
| 10,524,867 B2 | 1/2020 | Kokish et al. |
| 10,539,478 B2 | 1/2020 | Lin et al. |
| 10,543,047 B2 | 1/2020 | Yu |
| 10,543,048 B2 | 1/2020 | Noonan |
| 10,555,778 B2 | 2/2020 | Ummalaneni |
| 10,556,092 B2 | 2/2020 | Yu et al. |
| 10,569,052 B2 | 2/2020 | Kokish et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh et al. |
| 10,667,871 B2 | 6/2020 | Romo et al. |
| 10,667,875 B2 | 6/2020 | DeFonzo et al. |
| 10,682,189 B2 | 6/2020 | Schuh et al. |
| 10,687,903 B2 | 6/2020 | Lewis et al. |
| 10,695,536 B2 | 6/2020 | Weitzner et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho et al. |
| 10,779,898 B2 | 9/2020 | Hill et al. |
| 10,786,329 B2 | 9/2020 | Schuh et al. |
| 10,786,432 B2 | 9/2020 | Jornitz et al. |
| 10,792,112 B2 | 10/2020 | Kokish et al. |
| 10,792,464 B2 | 10/2020 | Romo et al. |
| 10,792,466 B2 | 10/2020 | Landey et al. |
| 10,813,539 B2 | 10/2020 | Graetzel et al. |
| 10,814,101 B2 | 10/2020 | Jiang |
| 10,820,947 B2 | 11/2020 | Julian |
| 10,820,952 B2 | 11/2020 | Yu |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,835,153 B2 | 11/2020 | Rafii-Tari et al. |
| 10,850,013 B2 | 12/2020 | Hsu et al. |
| 10,881,280 B2 | 1/2021 | Baez, Jr. |
| 10,888,386 B2 | 1/2021 | Eyre et al. |
| 10,898,276 B2 | 1/2021 | Graetzel et al. |
| 2001/0042643 A1 | 11/2001 | Krueger et al. |
| 2002/0019644 A1 | 2/2002 | Hastings et al. |
| 2002/0045905 A1 | 4/2002 | Gerbi et al. |
| 2002/0068954 A1 | 6/2002 | Foster |
| 2002/0098938 A1 | 7/2002 | Milbourne et al. |
| 2002/0100254 A1 | 8/2002 | Dharssi |
| 2002/0107573 A1 | 8/2002 | Steinberg |
| 2002/0111608 A1 | 8/2002 | Baerveldt et al. |
| 2002/0111621 A1 | 8/2002 | Wallace et al. |
| 2002/0117017 A1 | 8/2002 | Bernhardt et al. |
| 2002/0161355 A1 | 10/2002 | Wollschlager |
| 2002/0161426 A1 | 10/2002 | Iancea |
| 2002/0177789 A1 | 11/2002 | Ferry et al. |
| 2003/0004455 A1 | 1/2003 | Kadziauskas et al. |
| 2003/0040681 A1 | 2/2003 | Ng et al. |
| 2003/0056561 A1 | 3/2003 | Butscher et al. |
| 2003/0065358 A1 | 4/2003 | Frecker et al. |
| 2003/0088254 A1 | 5/2003 | Gregory et al. |
| 2003/0100882 A1 | 5/2003 | Beden et al. |
| 2003/0109780 A1 | 6/2003 | Coste-Maniere et al. |
| 2003/0109877 A1 | 6/2003 | Morley et al. |
| 2003/0109889 A1 | 6/2003 | Mercereau et al. |
| 2003/0158545 A1 | 8/2003 | Hovda et al. |
| 2003/0167623 A1 | 9/2003 | Lorenz |
| 2003/0208189 A1 | 11/2003 | Payman |
| 2003/0212308 A1 | 11/2003 | Bendall |
| 2003/0225419 A1 | 12/2003 | Lippitt et al. |
| 2004/0015053 A1 | 1/2004 | Bieger et al. |
| 2004/0122444 A1 | 6/2004 | Gerard |
| 2004/0143253 A1 | 7/2004 | Vanney et al. |
| 2004/0152972 A1 | 8/2004 | Hunter |
| 2004/0153093 A1 | 8/2004 | Donovan |
| 2004/0158261 A1 | 8/2004 | Vu |
| 2004/0186349 A1 | 9/2004 | Ewers et al. |
| 2004/0193146 A1 | 9/2004 | Lee et al. |
| 2004/0210116 A1 | 10/2004 | Nakao |
| 2004/0243147 A1 | 12/2004 | Lipow |
| 2004/0253079 A1 | 12/2004 | Sanchez |
| 2004/0254566 A1 | 12/2004 | Plicchi et al. |
| 2004/0260246 A1 | 12/2004 | Desmond |
| 2005/0004579 A1 | 1/2005 | Schneider et al. |
| 2005/0033270 A1 | 2/2005 | Ramans et al. |
| 2005/0054900 A1 | 3/2005 | Mawn et al. |
| 2005/0059645 A1 | 3/2005 | Bodor |
| 2005/0159645 A1 | 7/2005 | Bertolero et al. |
| 2005/0177026 A1 | 8/2005 | Hoeg et al. |
| 2005/0183532 A1 | 8/2005 | Najaf et al. |
| 2005/0222554 A1 | 10/2005 | Wallace et al. |
| 2005/0240178 A1 | 10/2005 | Morley et al. |
| 2005/0261705 A1 | 11/2005 | Gist |
| 2005/0267488 A1 | 12/2005 | Hare et al. |
| 2006/0015133 A1 | 1/2006 | Grayzel et al. |
| 2006/0041245 A1 | 2/2006 | Ferry et al. |
| 2006/0058813 A1 | 3/2006 | Teague et al. |
| 2006/0111692 A1 | 5/2006 | Hlavka et al. |
| 2006/0116693 A1 | 6/2006 | Weisenburgh et al. |
| 2006/0135963 A1 | 6/2006 | Kick et al. |
| 2006/0142657 A1 | 6/2006 | Quaid et al. |
| 2006/0146010 A1 | 7/2006 | Schneider |
| 2006/0156875 A1 | 7/2006 | McRury et al. |
| 2006/0161137 A1 | 7/2006 | Orban et al. |
| 2006/0189891 A1 | 8/2006 | Waxman et al. |
| 2006/0201688 A1 | 9/2006 | Jenner et al. |
| 2006/0229587 A1 | 10/2006 | Beyar et al. |
| 2006/0237205 A1 | 10/2006 | Sia et al. |
| 2007/0000498 A1 | 1/2007 | Glynn et al. |
| 2007/0000577 A1 | 1/2007 | Chen |
| 2007/0013336 A1 | 1/2007 | Nowlin et al. |
| 2007/0016164 A1 | 1/2007 | Dudney et al. |
| 2007/0021768 A1 | 1/2007 | Nance et al. |
| 2007/0027443 A1 | 2/2007 | Rose et al. |
| 2007/0027534 A1 | 2/2007 | Bergheim et al. |
| 2007/0032906 A1 | 2/2007 | Sutherland et al. |
| 2007/0060879 A1 | 3/2007 | Weitzner et al. |
| 2007/0086934 A1 | 4/2007 | Huber et al. |
| 2007/0100201 A1 | 5/2007 | Komiya et al. |
| 2007/0100254 A1 | 5/2007 | Murakami et al. |
| 2007/0106304 A1 | 5/2007 | Hammack et al. |
| 2007/0112355 A1 | 5/2007 | Salahieh et al. |
| 2007/0119274 A1 | 5/2007 | Devengenzo et al. |
| 2007/0123855 A1 | 5/2007 | Morley et al. |
| 2007/0135803 A1 | 6/2007 | Belson |
| 2007/0149946 A1 | 6/2007 | Viswanathan et al. |
| 2007/0185485 A1 | 8/2007 | Hauck et al. |
| 2007/0191177 A1 | 8/2007 | Nagai et al. |
| 2007/0203475 A1 | 8/2007 | Fischer et al. |
| 2007/0208252 A1 | 9/2007 | Makower |
| 2007/0208375 A1 | 9/2007 | Nishizawa et al. |
| 2007/0213668 A1 | 9/2007 | Spitz |
| 2007/0239028 A1 | 10/2007 | Houser et al. |
| 2007/0239178 A1 | 10/2007 | Weitzner et al. |
| 2007/0245175 A1 | 10/2007 | Zheng et al. |

(56) References Cited

U.S. PATENT DOCUMENTS

| | | |
|---|---|---|
| 2007/0250111 A1 | 10/2007 | Lu et al. |
| 2007/0299427 A1 | 12/2007 | Yeung et al. |
| 2008/0009884 A1 | 1/2008 | Kennedy |
| 2008/0015566 A1 | 1/2008 | Livneh |
| 2008/0021440 A1 | 1/2008 | Solomon |
| 2008/0027464 A1 | 1/2008 | Moll et al. |
| 2008/0033467 A1 | 2/2008 | Miyamoto et al. |
| 2008/0039255 A1 | 2/2008 | Jinno et al. |
| 2008/0045981 A1 | 2/2008 | Margolin et al. |
| 2008/0046122 A1 | 2/2008 | Manzo et al. |
| 2008/0065103 A1 | 3/2008 | Cooper et al. |
| 2008/0065111 A1 | 3/2008 | Blumenkranz et al. |
| 2008/0065112 A1 | 3/2008 | Tovey et al. |
| 2008/0082109 A1 | 4/2008 | Moll et al. |
| 2008/0091215 A1 | 4/2008 | Saleh |
| 2008/0125698 A1 | 5/2008 | Gerg et al. |
| 2008/0147011 A1 | 6/2008 | Urmey |
| 2008/0177277 A1 | 7/2008 | Huang et al. |
| 2008/0177285 A1 | 7/2008 | Brock et al. |
| 2008/0187101 A1 | 8/2008 | Gertner |
| 2008/0188864 A1 | 8/2008 | Ducharme |
| 2008/0196533 A1 | 8/2008 | Bergamasco et al. |
| 2008/0214925 A1 | 9/2008 | Wilson et al. |
| 2008/0228104 A1 | 9/2008 | Uber et al. |
| 2008/0243064 A1 | 10/2008 | Stahler et al. |
| 2008/0249536 A1 | 10/2008 | Stahler et al. |
| 2008/0253108 A1 | 10/2008 | Ellenburg et al. |
| 2008/0262301 A1 | 10/2008 | Gibbons et al. |
| 2008/0262480 A1 | 10/2008 | Stahler et al. |
| 2008/0262513 A1 | 10/2008 | Stahler et al. |
| 2008/0287963 A1 | 11/2008 | Rogers et al. |
| 2008/0300592 A1 | 12/2008 | Weitzner et al. |
| 2008/0302200 A1 | 12/2008 | Tobey |
| 2008/0312521 A1 | 12/2008 | Solomon |
| 2009/0005768 A1 | 1/2009 | Sharareh et al. |
| 2009/0012507 A1 | 1/2009 | Culbertson et al. |
| 2009/0030446 A1 | 1/2009 | Measamer |
| 2009/0036900 A1 | 2/2009 | Moll |
| 2009/0043305 A1 | 2/2009 | Brodbeck et al. |
| 2009/0062602 A1 | 3/2009 | Rosenberg et al. |
| 2009/0082634 A1 | 3/2009 | Kathrani et al. |
| 2009/0082722 A1 | 3/2009 | Munger et al. |
| 2009/0088774 A1 | 4/2009 | Swarup et al. |
| 2009/0098971 A1 | 4/2009 | Ho et al. |
| 2009/0105645 A1 | 4/2009 | Kidd et al. |
| 2009/0105723 A1 | 4/2009 | Dillinger |
| 2009/0131885 A1 | 5/2009 | Akahoshi |
| 2009/0138025 A1 | 5/2009 | Stahler et al. |
| 2009/0161827 A1 | 6/2009 | Gertner et al. |
| 2009/0163948 A1 | 6/2009 | Sunaoshi et al. |
| 2009/0171371 A1 | 7/2009 | Nixon et al. |
| 2009/0192510 A1 | 7/2009 | Bahney |
| 2009/0192524 A1 | 7/2009 | Itkowitz et al. |
| 2009/0227998 A1 | 9/2009 | Aljuri et al. |
| 2009/0247944 A1 | 10/2009 | Kirschenman et al. |
| 2009/0248039 A1 | 10/2009 | Cooper et al. |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0270760 A1 | 10/2009 | Leimbach et al. |
| 2009/0287188 A1 | 11/2009 | Golden et al. |
| 2009/0299352 A1 | 12/2009 | Zerfas et al. |
| 2009/0312773 A1 | 12/2009 | Cabrera et al. |
| 2010/0004642 A1 | 1/2010 | Lumpkin |
| 2010/0010504 A1 | 1/2010 | Simaan et al. |
| 2010/0011900 A1 | 1/2010 | Burbank |
| 2010/0011901 A1 | 1/2010 | Burbank |
| 2010/0016852 A1 | 1/2010 | Manzo et al. |
| 2010/0016853 A1 | 1/2010 | Burbank |
| 2010/0030023 A1 | 2/2010 | Yoshie |
| 2010/0069833 A1 | 3/2010 | Wenderow et al. |
| 2010/0073150 A1 | 3/2010 | Olson et al. |
| 2010/0081965 A1 | 4/2010 | Mugan et al. |
| 2010/0082017 A1 | 4/2010 | Zickler et al. |
| 2010/0082041 A1 | 4/2010 | Prisco |
| 2010/0125284 A1 | 5/2010 | Tanner et al. |
| 2010/0130923 A1 | 5/2010 | Cleary et al. |
| 2010/0130987 A1 | 5/2010 | Wenderow et al. |
| 2010/0137846 A1 | 6/2010 | Desai et al. |
| 2010/0175701 A1 | 7/2010 | Reis et al. |
| 2010/0179632 A1 | 7/2010 | Bruszewski et al. |
| 2010/0204605 A1 | 8/2010 | Blakley et al. |
| 2010/0204646 A1 | 8/2010 | Plicchi et al. |
| 2010/0210923 A1 | 8/2010 | Li et al. |
| 2010/0217235 A1 | 8/2010 | Thorstenson et al. |
| 2010/0225209 A1 | 9/2010 | Goldberg et al. |
| 2010/0228191 A1 | 9/2010 | Alvarez et al. |
| 2010/0228249 A1 | 9/2010 | Mohr et al. |
| 2010/0248177 A1 | 9/2010 | Mangelberger et al. |
| 2010/0249506 A1 | 9/2010 | Prisco |
| 2010/0268211 A1 | 10/2010 | Manwaring et al. |
| 2010/0274078 A1 | 10/2010 | Kim et al. |
| 2010/0312141 A1 | 12/2010 | Keast et al. |
| 2010/0331856 A1 | 12/2010 | Carlson et al. |
| 2010/0331858 A1 | 12/2010 | Simaan et al. |
| 2010/0332033 A1 | 12/2010 | Diolaiti et al. |
| 2011/0009863 A1 | 1/2011 | Marczyk et al. |
| 2011/0015483 A1 | 1/2011 | Barbagli et al. |
| 2011/0015484 A1 | 1/2011 | Alvarez et al. |
| 2011/0015648 A1 | 1/2011 | Alvarez et al. |
| 2011/0015650 A1 | 1/2011 | Choi et al. |
| 2011/0028790 A1 | 2/2011 | Farr et al. |
| 2011/0028991 A1 | 2/2011 | Ikeda et al. |
| 2011/0071541 A1 | 3/2011 | Prisco et al. |
| 2011/0071543 A1 | 3/2011 | Prisco et al. |
| 2011/0106146 A1 | 5/2011 | Jeong |
| 2011/0125165 A1 | 5/2011 | Simaan et al. |
| 2011/0130718 A1 | 6/2011 | Kidd et al. |
| 2011/0147030 A1 | 6/2011 | Blum et al. |
| 2011/0152880 A1 | 6/2011 | Alvarez et al. |
| 2011/0160713 A1 | 6/2011 | Neuberger |
| 2011/0160745 A1 | 6/2011 | Fielding et al. |
| 2011/0167611 A1 | 7/2011 | Williams |
| 2011/0184391 A1 | 7/2011 | Aljuri et al. |
| 2011/0208211 A1 | 8/2011 | Whitfield et al. |
| 2011/0213362 A1 | 9/2011 | Cunningham et al. |
| 2011/0224660 A1 | 9/2011 | Neuberger et al. |
| 2011/0238064 A1 | 9/2011 | Williams |
| 2011/0238083 A1 | 9/2011 | Moll et al. |
| 2011/0257641 A1 | 10/2011 | Hastings et al. |
| 2011/0261183 A1 | 10/2011 | Ma et al. |
| 2011/0270273 A1 | 11/2011 | Moll et al. |
| 2011/0276085 A1 | 11/2011 | Krzyzanowski |
| 2011/0277775 A1 | 11/2011 | Holop et al. |
| 2011/0288573 A1 | 11/2011 | Yates et al. |
| 2011/0306836 A1 | 12/2011 | Ohline et al. |
| 2011/0313343 A1 | 12/2011 | Milutinovic et al. |
| 2012/0048759 A1 | 3/2012 | Disch et al. |
| 2012/0069167 A1 | 3/2012 | Liu et al. |
| 2012/0071821 A1 | 3/2012 | Yu |
| 2012/0071894 A1 | 3/2012 | Tanner et al. |
| 2012/0071895 A1 | 3/2012 | Stahler et al. |
| 2012/0132018 A1 | 5/2012 | Tang et al. |
| 2012/0136419 A1 | 5/2012 | Zarembo et al. |
| 2012/0138586 A1 | 6/2012 | Webster et al. |
| 2012/0138660 A1 | 6/2012 | Shelton, IV |
| 2012/0143226 A1 | 6/2012 | Belson et al. |
| 2012/0150154 A1 | 6/2012 | Brisson et al. |
| 2012/0186194 A1 | 7/2012 | Schlieper |
| 2012/0191107 A1 | 7/2012 | Tanner et al. |
| 2012/0209315 A1 | 8/2012 | Girbau |
| 2012/0217457 A1 | 8/2012 | Schena et al. |
| 2012/0232342 A1 | 9/2012 | Reydel |
| 2012/0232476 A1 | 9/2012 | Bhat et al. |
| 2012/0239012 A1 | 9/2012 | Laurent et al. |
| 2012/0253277 A1 | 10/2012 | Tah et al. |
| 2012/0253332 A1 | 10/2012 | Moll |
| 2012/0259320 A1 | 10/2012 | Loesel et al. |
| 2012/0277730 A1 | 11/2012 | Salahieh et al. |
| 2012/0283747 A1 | 11/2012 | Popovic |
| 2012/0296318 A1 | 11/2012 | Wellhöfer et al. |
| 2013/0006144 A1 | 1/2013 | Clancy et al. |
| 2013/0018400 A1 | 1/2013 | Milton et al. |
| 2013/0035537 A1 | 2/2013 | Wallace et al. |

(56) References Cited

U.S. PATENT DOCUMENTS

| | | |
|---|---|---|
| 2013/0053877 A1 | 2/2013 | BenMaamer et al. |
| 2013/0066136 A1 | 3/2013 | Palese et al. |
| 2013/0066335 A1 | 3/2013 | Bärwinkel et al. |
| 2013/0085442 A1 | 4/2013 | Shtul et al. |
| 2013/0085486 A1 | 4/2013 | Boutoussov et al. |
| 2013/0096422 A1 | 4/2013 | Boctor et al. |
| 2013/0096574 A1 | 4/2013 | Kang et al. |
| 2013/0110042 A1 | 5/2013 | Humphreys |
| 2013/0110107 A1 | 5/2013 | Smith et al. |
| 2013/0116716 A1 | 5/2013 | Bahls et al. |
| 2013/0144116 A1 | 6/2013 | Cooper et al. |
| 2013/0144274 A1 | 6/2013 | Stefanchik et al. |
| 2013/0144395 A1 | 6/2013 | Stefanchik et al. |
| 2013/0190741 A1 | 7/2013 | Moll et al. |
| 2013/0190796 A1 | 7/2013 | Tilson et al. |
| 2013/0204124 A1 | 8/2013 | Duindam et al. |
| 2013/0225997 A1 | 8/2013 | Dillard et al. |
| 2013/0226151 A1 | 8/2013 | Suehara |
| 2013/0226161 A1 | 8/2013 | Hickenbotham |
| 2013/0231678 A1 | 9/2013 | Wenderow et al. |
| 2013/0233908 A1 | 9/2013 | Knodel et al. |
| 2013/0253267 A1 | 9/2013 | Collins |
| 2013/0303876 A1 | 11/2013 | Gelfand et al. |
| 2013/0304084 A1 | 11/2013 | Beira et al. |
| 2013/0310819 A1 | 11/2013 | Neuberger et al. |
| 2013/0317519 A1 | 11/2013 | Romo et al. |
| 2013/0334281 A1 | 12/2013 | Williams |
| 2013/0345519 A1 | 12/2013 | Piskun et al. |
| 2013/0345686 A1 | 12/2013 | Brown |
| 2014/0000411 A1 | 1/2014 | Shelton, IV et al. |
| 2014/0005681 A1 | 1/2014 | Gee et al. |
| 2014/0039517 A1 | 2/2014 | Bowling et al. |
| 2014/0039681 A1 | 2/2014 | Bowling et al. |
| 2014/0046308 A1 | 2/2014 | Bischoff et al. |
| 2014/0051985 A1 | 2/2014 | Fan et al. |
| 2014/0058365 A1 | 2/2014 | Bille et al. |
| 2014/0058404 A1 | 2/2014 | Hammack et al. |
| 2014/0058428 A1 | 2/2014 | Christopher et al. |
| 2014/0582428 | 2/2014 | Christopher et al. |
| 2014/0066944 A1 | 3/2014 | Taylor et al. |
| 2014/0069437 A1 | 3/2014 | Reis et al. |
| 2014/0100445 A1 | 4/2014 | Stenzel et al. |
| 2014/0142591 A1 | 5/2014 | Alvarez et al. |
| 2014/0163318 A1 | 6/2014 | Swanstrom |
| 2014/0163736 A1 | 6/2014 | Azizian et al. |
| 2014/0166023 A1 | 6/2014 | Kishi |
| 2014/0171778 A1 | 6/2014 | Tsusaka et al. |
| 2014/0180063 A1 | 6/2014 | Zhao et al. |
| 2014/0194859 A1 | 7/2014 | Ianchulev |
| 2014/0194905 A1 | 7/2014 | Kappel et al. |
| 2014/0222019 A1 | 8/2014 | Brudniok |
| 2014/0222207 A1 | 8/2014 | Bowling et al. |
| 2014/0243849 A1 | 8/2014 | Saglam et al. |
| 2014/0246473 A1 | 9/2014 | Auld |
| 2014/0257333 A1 | 9/2014 | Blumenkranz |
| 2014/0275956 A1 | 9/2014 | Fan |
| 2014/0276233 A1 | 9/2014 | Murphy |
| 2014/0276389 A1 | 9/2014 | Walker |
| 2014/0276394 A1 | 9/2014 | Wong et al. |
| 2014/0276594 A1 | 9/2014 | Tanner et al. |
| 2014/0276723 A1 | 9/2014 | Parihar et al. |
| 2014/0276935 A1 | 9/2014 | Yu |
| 2014/0276936 A1 | 9/2014 | Kokish et al. |
| 2014/0276956 A1 | 9/2014 | Crainich et al. |
| 2014/0277334 A1 | 9/2014 | Yu et al. |
| 2014/0309649 A1 | 10/2014 | Alvarez et al. |
| 2014/0309655 A1 | 10/2014 | Gal et al. |
| 2014/0316203 A1 | 10/2014 | Carroux et al. |
| 2014/0357984 A1 | 12/2014 | Wallace et al. |
| 2014/0364870 A1 | 12/2014 | Alvarez et al. |
| 2014/0375784 A1 | 12/2014 | Massetti |
| 2014/0379000 A1 | 12/2014 | Romo et al. |
| 2015/0012134 A1 | 1/2015 | Robinson et al. |
| 2015/0028195 A1 | 1/2015 | King et al. |
| 2015/0051592 A1 | 2/2015 | Kintz et al. |
| 2015/0073439 A1 | 3/2015 | Dannaher |
| 2015/0080879 A1 | 3/2015 | Trees et al. |
| 2015/0090063 A1 | 4/2015 | Lantermann et al. |
| 2015/0101442 A1 | 4/2015 | Romo et al. |
| 2015/0119634 A1 | 4/2015 | Jones |
| 2015/0119638 A1 | 4/2015 | Yu et al. |
| 2015/0127045 A1 | 5/2015 | Prestel |
| 2015/0133960 A1 | 5/2015 | Lohmeier et al. |
| 2015/0133963 A1 | 5/2015 | Barbagli |
| 2015/0142013 A1 | 5/2015 | Tanner et al. |
| 2015/0144514 A1 | 5/2015 | Brennan et al. |
| 2015/0148600 A1 | 5/2015 | Ashinuma et al. |
| 2015/0150635 A1 | 6/2015 | Kilroy et al. |
| 2015/0164522 A1 | 6/2015 | Budiman et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0182250 A1 | 7/2015 | Conlon et al. |
| 2015/0190204 A1 | 7/2015 | Popovi |
| 2015/0201917 A1 | 7/2015 | Snow |
| 2015/0202085 A1 | 7/2015 | Lemonis et al. |
| 2015/0231364 A1 | 8/2015 | Blanchard et al. |
| 2015/0314110 A1 | 11/2015 | Park |
| 2015/0335480 A1 | 11/2015 | Alvarez et al. |
| 2015/0366629 A1 | 12/2015 | Bowling et al. |
| 2015/0374445 A1 | 12/2015 | Gombert et al. |
| 2015/0374446 A1 | 12/2015 | Malackowski et al. |
| 2016/0000512 A1 | 1/2016 | Gombert et al. |
| 2016/0001038 A1 | 1/2016 | Romo et al. |
| 2016/0022289 A1 | 1/2016 | Wan |
| 2016/0022466 A1 | 1/2016 | Pedtke et al. |
| 2016/0030073 A1 | 2/2016 | Isakov et al. |
| 2016/0045208 A1 | 2/2016 | Ciulla |
| 2016/0051318 A1 | 2/2016 | Manzo et al. |
| 2016/0066935 A1 | 3/2016 | Nguyen et al. |
| 2016/0124220 A1 | 5/2016 | Bueeler et al. |
| 2016/0151122 A1 | 6/2016 | Alvarez et al. |
| 2016/0157945 A1 | 6/2016 | Madhani et al. |
| 2016/0158490 A1 | 6/2016 | Leeflang et al. |
| 2016/0166234 A1 | 6/2016 | Zhang et al. |
| 2016/0183841 A1 | 6/2016 | Duindam et al. |
| 2016/0184032 A1 | 6/2016 | Romo et al. |
| 2016/0192860 A1 | 7/2016 | Allenby et al. |
| 2016/0199984 A1 | 7/2016 | Lohmeier et al. |
| 2016/0206389 A1 | 7/2016 | Miller et al. |
| 2016/0213435 A1 | 7/2016 | Hourtash et al. |
| 2016/0235478 A1 | 8/2016 | Bonneau et al. |
| 2016/0235495 A1 | 8/2016 | Wallace et al. |
| 2016/0242858 A1 | 8/2016 | Barrera et al. |
| 2016/0249932 A1 | 9/2016 | Rogers et al. |
| 2016/0270865 A1 | 9/2016 | Landey et al. |
| 2016/0270866 A1 | 9/2016 | Yu et al. |
| 2016/0279394 A1 | 9/2016 | Moll et al. |
| 2016/0287279 A1 | 10/2016 | Bovay et al. |
| 2016/0287840 A1 | 10/2016 | Jiang |
| 2016/0296294 A1 | 10/2016 | Moll et al. |
| 2016/0302871 A1 | 10/2016 | Gregerson et al. |
| 2016/0303743 A1 | 10/2016 | Rockrohr |
| 2016/0310146 A1 | 10/2016 | Levy et al. |
| 2016/0331358 A1 | 11/2016 | Gordon |
| 2016/0338783 A1 | 11/2016 | Romo et al. |
| 2016/0338785 A1 | 11/2016 | Kokish et al. |
| 2016/0346049 A1 | 12/2016 | Allen et al. |
| 2016/0367324 A1 | 12/2016 | Sato et al. |
| 2016/0374541 A1 | 12/2016 | Agrawal et al. |
| 2017/0000577 A1 | 1/2017 | Bowling et al. |
| 2017/0007279 A1 | 1/2017 | Sharma |
| 2017/0007337 A1 | 1/2017 | Dan |
| 2017/0020615 A1 | 1/2017 | Koenig et al. |
| 2017/0049471 A1 | 2/2017 | Gaffney et al. |
| 2017/0055995 A1 | 3/2017 | Weir et al. |
| 2017/0065227 A1 | 3/2017 | Marrs et al. |
| 2017/0065357 A1 | 3/2017 | Schuh |
| 2017/0065363 A1 | 3/2017 | Schuh et al. |
| 2017/0065364 A1 | 3/2017 | Schuh et al. |
| 2017/0065365 A1 | 3/2017 | Schuh |
| 2017/0071584 A1 | 3/2017 | Suigetsu et al. |
| 2017/0086934 A1 | 3/2017 | Devengenzo et al. |
| 2017/0095234 A1 | 4/2017 | Prisco et al. |

(56) References Cited

U.S. PATENT DOCUMENTS

| | | |
|---|---|---|
| 2017/0095295 A1 | 4/2017 | Overmyer |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0135706 A1 | 5/2017 | Frey et al. |
| 2017/0151028 A1 | 6/2017 | Ogawa et al. |
| 2017/0151416 A1 | 6/2017 | Kutikov et al. |
| 2017/0165009 A1 | 6/2017 | Chaplin et al. |
| 2017/0165011 A1 | 6/2017 | Bovay et al. |
| 2017/0172553 A1 | 6/2017 | Chaplin et al. |
| 2017/0172673 A1 | 6/2017 | Yu et al. |
| 2017/0172680 A1 | 6/2017 | Bowling et al. |
| 2017/0202627 A1 | 7/2017 | Sramek et al. |
| 2017/0202827 A1 | 7/2017 | Genkin et al. |
| 2017/0209073 A1 | 7/2017 | Sramek et al. |
| 2017/0252096 A1 | 9/2017 | Felder et al. |
| 2017/0258534 A1 | 9/2017 | Hourtash et al. |
| 2017/0265923 A1 | 9/2017 | Privitera et al. |
| 2017/0265954 A1 | 9/2017 | Burbank et al. |
| 2017/0281049 A1 | 10/2017 | Yamamoto et al. |
| 2017/0290631 A1 | 10/2017 | Lee et al. |
| 2017/0319289 A1 | 11/2017 | Neff |
| 2017/0325932 A1 | 11/2017 | Hoelzle |
| 2017/0333147 A1 | 11/2017 | Bernstein |
| 2017/0333679 A1 | 11/2017 | Jiang et al. |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0000563 A1 | 1/2018 | Shanjani et al. |
| 2018/0025666 A1 | 1/2018 | Ho et al. |
| 2018/0042464 A1 | 2/2018 | Arai et al. |
| 2018/0042686 A1 | 2/2018 | Peine |
| 2018/0049792 A1 | 2/2018 | Eckert et al. |
| 2018/0049824 A1 | 2/2018 | Harris et al. |
| 2018/0055583 A1 | 3/2018 | Schuh et al. |
| 2018/0056044 A1 | 3/2018 | Choi et al. |
| 2018/0079090 A1 | 3/2018 | Koenig et al. |
| 2018/0080841 A1 | 3/2018 | Cordoba et al. |
| 2018/0104820 A1 | 4/2018 | Troy et al. |
| 2018/0116735 A1 | 5/2018 | Tierney et al. |
| 2018/0140371 A1 | 5/2018 | Hares et al. |
| 2018/0168681 A1 | 6/2018 | Kirk et al. |
| 2018/0177383 A1 | 6/2018 | Noonan et al. |
| 2018/0177556 A1 | 6/2018 | Noonan |
| 2018/0177561 A1 | 6/2018 | Mintz et al. |
| 2018/0193049 A1 | 7/2018 | Heck et al. |
| 2018/0206927 A1 | 7/2018 | Prisco et al. |
| 2018/0206931 A1 | 7/2018 | Scheib |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0243048 A1 | 8/2018 | Shan et al. |
| 2018/0250083 A1 | 9/2018 | Schuh et al. |
| 2018/0250085 A1 | 9/2018 | Simi et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289431 A1 | 10/2018 | Draper et al. |
| 2018/0296285 A1 | 10/2018 | Simi et al. |
| 2018/0296299 A1 | 10/2018 | Iceman |
| 2018/0303566 A1 | 10/2018 | Soundararajan et al. |
| 2018/0325499 A1 | 11/2018 | Landey et al. |
| 2018/0326181 A1 | 11/2018 | Kokish et al. |
| 2018/0333044 A1 | 11/2018 | Jenkins |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000576 A1 | 1/2019 | Mintz et al. |
| 2019/0015166 A1 | 1/2019 | Mahoney et al. |
| 2019/0017320 A1 | 1/2019 | Lombardini |
| 2019/0069962 A1 | 3/2019 | Tabandeh et al. |
| 2019/0083183 A1 | 3/2019 | Moll et al. |
| 2019/0099231 A1 | 4/2019 | Bruehwiler et al. |
| 2019/0099232 A1 | 4/2019 | Soto et al. |
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0117324 A1 | 4/2019 | Hibner et al. |
| 2019/0125465 A1 | 5/2019 | Evans et al. |
| 2019/0142537 A1 | 5/2019 | Covington |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0191967 A1 | 6/2019 | Yamamoto et al. |
| 2019/0192249 A1 | 6/2019 | Bowling et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223967 A1 | 7/2019 | Abbott et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0231458 A1 | 8/2019 | DiMaio et al. |
| 2019/0231460 A1 | 8/2019 | DiMaio et al. |
| 2019/0239890 A1 | 8/2019 | Stokes et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298464 A1 | 10/2019 | Abbott |
| 2019/0298465 A1 | 10/2019 | Chin et al. |
| 2019/0298469 A1 | 10/2019 | Ramstad et al. |
| 2019/0314616 A1 | 10/2019 | Moll et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000533 A1 | 1/2020 | Schuh et al. |
| 2020/0000855 A1 | 1/2020 | Xu et al. |
| 2020/0008874 A1 | 1/2020 | Barbagli et al. |
| 2020/0022767 A1 | 1/2020 | Hill et al. |
| 2020/0030046 A1 | 1/2020 | Bowling et al. |
| 2020/0034526 A1 | 1/2020 | Asokan et al. |
| 2020/0038123 A1 | 2/2020 | Graetzel et al. |
| 2020/0039086 A1 | 2/2020 | Meyer et al. |
| 2020/0040537 A1 | 2/2020 | Groeneweg |
| 2020/0046434 A1 | 2/2020 | Graetzel et al. |
| 2020/0054408 A1 | 2/2020 | Schuh et al. |
| 2020/0055801 A1 | 2/2020 | Fish et al. |
| 2020/0060516 A1 | 2/2020 | Baez, Jr. et al. |
| 2020/0085516 A1 | 3/2020 | DeFonzo et al. |
| 2020/0086087 A1 | 3/2020 | Hart et al. |
| 2020/0091799 A1 | 3/2020 | Covington et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0129252 A1 | 4/2020 | Kokish et al. |
| 2020/0138531 A1 | 5/2020 | Chaplin |
| 2020/0146769 A1 | 5/2020 | Eyre et al. |
| 2020/0155245 A1 | 5/2020 | Yu |

(56) References Cited

U.S. PATENT DOCUMENTS

| | | | |
|---|---|---|---|
| 2020/0163726 A1 | 5/2020 | Tanner et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197109 A1 | 6/2020 | Chaplin |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0230360 A1 | 7/2020 | Yu et al. |
| 2020/0237458 A1 | 7/2020 | Defonzo et al. |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |
| 2020/0297437 A1 | 9/2020 | Schuh et al. |
| 2020/0297444 A1 | 9/2020 | Camarillo et al. |
| 2020/0305922 A1 | 10/2020 | Yan et al. |
| 2020/0305983 A1 | 10/2020 | Yampolsky et al. |
| 2020/0305989 A1 | 10/2020 | Schuh et al. |
| 2020/0305992 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2020/0345216 A1 | 11/2020 | Jenkins |
| 2020/0352420 A1 | 11/2020 | Graetzel et al. |
| 2020/0360183 A1 | 11/2020 | Alvarez et al. |
| 2020/0367726 A1 | 11/2020 | Landey et al. |
| 2020/0367981 A1 | 11/2020 | Ho et al. |
| 2020/0375678 A1 | 12/2020 | Wallace et al. |
| 2020/0383735 A1 | 12/2020 | Lewis et al. |
| 2020/0405411 A1 | 12/2020 | Draper et al. |
| 2020/0405413 A1 | 12/2020 | Kokish et al. |
| 2020/0405419 A1 | 12/2020 | Mao et al. |
| 2020/0405420 A1 | 12/2020 | Purohit et al. |
| 2020/0405423 A1 | 12/2020 | Schuh |
| 2020/0405424 A1 | 12/2020 | Schuh |
| 2020/0405434 A1 | 12/2020 | Schuh et al. |
| 2020/0406002 A1 | 12/2020 | Romo et al. |
| 2021/0007819 A1 | 1/2021 | Schuh et al. |
| 2021/0008341 A1 | 1/2021 | Landey et al. |
| 2021/0045819 A1 | 2/2021 | Castillo et al. |
| 2021/0045822 A1 | 2/2021 | Landey et al. |
| 2021/0045823 A1 | 2/2021 | Landey et al. |
| 2021/0045824 A1 | 2/2021 | Landey et al. |
| 2021/0059766 A1 | 3/2021 | Graetzel et al. |
| 2021/0121052 A1 | 4/2021 | Graetzel et al. |
| 2021/0169588 A1 | 6/2021 | Graetzel et al. |
| 2021/0178032 A1 | 6/2021 | Hsu et al. |
| 2021/0196293 A1 | 7/2021 | Lin et al. |
| 2021/0196312 A1 | 7/2021 | Plewe et al. |
| 2021/0196399 A1 | 7/2021 | Ayvali et al. |
| 2021/0196410 A1 | 7/2021 | Hsu et al. |

FOREIGN PATENT DOCUMENTS

| | | | |
|---|---|---|---|
| AU | 2018290831 A1 | 12/2019 |
| AU | 2018292606 A1 | 1/2020 |
| AU | 2018347472 A1 | 4/2020 |
| AU | 2018378808 A1 | 5/2020 |
| AU | 2019347767 A1 | 4/2021 |
| AU | 2021204979 A1 | 8/2021 |
| CN | 101161426 A | 4/2008 |
| CN | 101443069 A | 5/2009 |
| CN | 100515347 C | 7/2009 |
| CN | 101495023 A | 7/2009 |
| CN | 102015759 A | 4/2011 |
| CN | 201884596 U | 6/2011 |
| CN | 102316817 A | 1/2012 |
| CN | 102327118 A | 1/2012 |
| CN | 102458295 A | 5/2012 |
| CN | 102665590 A | 9/2012 |
| CN | 102834043 A | 12/2012 |
| CN | 102973317 A | 3/2013 |
| CN | 103037799 A | 4/2013 |
| CN | 103298414 A | 9/2013 |
| CN | 103735313 A | 4/2014 |
| CN | 104619281 A | 5/2015 |
| CN | 102947730 B | 7/2015 |
| CN | 105005103 A | 10/2015 |
| CN | 105147393 A | 12/2015 |
| CN | 105559850 A | 5/2016 |
| CN | 105559886 A | 5/2016 |
| CN | 205729413 U | 11/2016 |
| CN | 108882837 A | 11/2018 |
| CN | 108990412 A | 12/2018 |
| CN | 110831653 A | 2/2020 |
| CN | 110868903 A | 3/2020 |
| CN | 110891514 A | 3/2020 |
| CN | 111386450 A | 7/2020 |
| CN | 111432856 A | 7/2020 |
| CN | 112472007 A | 3/2021 |
| CN | 108369450 B | 4/2021 |
| CN | 112770690 A | 5/2021 |
| CN | 112804946 A | 5/2021 |
| DE | 19649082 C1 | 1/1998 |
| DE | 102004020465 | 9/2005 |
| DE | 102015016152 A1 | 6/2017 |
| EP | 1321106 A1 | 6/2003 |
| EP | 1442720 A1 | 8/2004 |
| EP | 1321106 B1 | 10/2005 |
| EP | 1849423 A2 | 10/2007 |
| EP | 1849423 A3 | 12/2007 |
| EP | 2043501 A2 | 4/2009 |
| EP | 2046227 A2 | 4/2009 |
| EP | 2210066 A2 | 7/2010 |
| EP | 2239600 A1 | 10/2010 |
| EP | 2567670 A1 | 3/2013 |
| EP | 3025630 A1 | 6/2016 |
| EP | 3387514 B1 | 6/2019 |
| EP | 3518724 A1 | 8/2019 |
| EP | 2577363 B1 | 7/2020 |
| EP | 3676587 A1 | 7/2020 |
| EP | 3752085 A1 | 12/2020 |
| EP | 3600031 A4 | 1/2021 |
| EP | 3644820 A4 | 3/2021 |
| EP | 3645100 A4 | 3/2021 |
| EP | 3820373 A1 | 5/2021 |
| EP | 3856064 A1 | 8/2021 |
| EP | 3684438 A4 | 9/2021 |
| JP | 07136173 | 5/1995 |
| JP | 2005270464 A | 10/2005 |
| JP | 2009139187 A | 6/2009 |
| JP | 2010046384 A | 3/2010 |
| JP | 2014159071 A | 9/2014 |
| JP | 2015181495 A | 10/2015 |
| JP | 2020512102 A | 4/2020 |
| JP | 2020526252 A | 8/2020 |
| JP | 2020526254 A | 8/2020 |
| JP | 2019531807 | 11/2020 |
| JP | 2020536754 A | 12/2020 |
| JP | 2021505287 A | 2/2021 |
| JP | 2021513436 A | 5/2021 |
| KR | 1020190119541 A | 10/2019 |
| KR | 20190134968 A | 12/2019 |
| KR | 20200023640 A | 3/2020 |
| KR | 20200024873 A | 3/2020 |
| KR | 20200071744 A | 6/2020 |
| KR | 20200099127 A | 8/2020 |
| KR | 20200122337 A | 10/2020 |
| KR | 20210042134 A | 4/2021 |
| KR | 20210073542 A | 6/2021 |
| KR | 102297011 B1 | 9/2021 |
| WO | 9414494 A2 | 7/1994 |
| WO | 9622591 A1 | 7/1996 |
| WO | 200274178 | 9/2002 |
| WO | 2007005976 A1 | 1/2007 |
| WO | 2007088208 A1 | 8/2007 |
| WO | 2007146987 A2 | 12/2007 |
| WO | 2008014425 A2 | 1/2008 |
| WO | 2008031077 A2 | 3/2008 |
| WO | 2008017080 A3 | 10/2008 |
| WO | 2008157399 A1 | 12/2008 |

(56) References Cited

FOREIGN PATENT DOCUMENTS

| | | | |
|---|---|---|---|
| WO | 2008101228 A3 | 1/2009 |
| WO | 2009023801 A1 | 2/2009 |
| WO | 2009064629 A2 | 5/2009 |
| WO | 2009092059 A2 | 7/2009 |
| WO | 2010133982 A2 | 11/2010 |
| WO | 2010133982 A3 | 1/2011 |
| WO | 2011005335 A1 | 1/2011 |
| WO | 2011008922 A2 | 1/2011 |
| WO | 2011150526 A1 | 12/2011 |
| WO | 2011161218 A1 | 12/2011 |
| WO | 2012037506 A2 | 3/2012 |
| WO | 2012167043 A3 | 1/2013 |
| WO | 2013107468 A1 | 7/2013 |
| WO | 2013130895 A1 | 9/2013 |
| WO | 2013179600 A1 | 12/2013 |
| WO | 2015127231 A1 | 8/2015 |
| WO | 2015153174 A1 | 10/2015 |
| WO | 2016137612 A1 | 9/2016 |
| WO | 2017059412 A1 | 4/2017 |
| WO | 2017075574 A1 | 5/2017 |
| WO | 2017097399 A1 | 6/2017 |
| WO | 2017114855 A1 | 7/2017 |
| WO | 2017151993 A1 | 9/2017 |
| WO | 20171156070 | 9/2017 |
| WO | 2018064394 A1 | 4/2018 |
| WO | 2018069679 A1 | 4/2018 |
| WO | 2018094191 A1 | 5/2018 |
| WO | 2018183727 A1 | 10/2018 |
| WO | 2018189722 A1 | 10/2018 |
| WO | 2019005872 A1 | 1/2019 |
| WO | 2019005992 A1 | 1/2019 |
| WO | 2019074669 A1 | 4/2019 |
| WO | 2019113389 A1 | 6/2019 |
| WO | 2019160865 A1 | 8/2019 |
| WO | 2020033318 A1 | 2/2020 |
| WO | 2020069430 A1 | 4/2020 |
| WO | 2021028889 A1 | 2/2021 |
| WO | 2021044297 A1 | 3/2021 |
| WO | 2021137071 A1 | 7/2021 |
| WO | 2021137106 A1 | 7/2021 |
| WO | 2021137108 A1 | 7/2021 |
| WO | 2021137109 A1 | 7/2021 |

OTHER PUBLICATIONS

Written opinion for PCT/IB2020/061905, dated Mar. 18, 2021, 6 pages.
Invitation to Pay Additional Fees in PCT appl No. PCT/US16/059686, dated Dec. 8, 2016.
Office action for U.S. Appl. No. 15/948,351, dated May 10, 2021, 11 pages.
Office action for U.S. Appl. No. 15/948,369, dated May 25, 2021, 14 pages.
Office action for U.S. Appl. No. 15/948,369, dated Nov. 20, 2020, 14 pages.
Advisory action for U.S. Appl. No. 15/948,351, dated Sep. 1, 2021, 3 pages.
AU Examination report for appl. No. 2016343849, dated Mar. 16, 2021, 5 pages.
Extended European Search Report for appl No. 16861031.9, dated Jun. 12, 2019.
Hernansanz et al., 2015, A multi-robot cooperation strategy for dexterous task oriented teleoperation, 2015, ELSEVIER, Robotics and Autonomous Systems, 68(205):156-172.
International search report and written opinion for appl No. PCTIB2020057704, dated Dec. 18, 2020, 11 pages.
JP office action dated Dec. 1, 2020, for patent appl No. 2018-521951, 4 pages.
Mayo Clinic, Robotic Surgery, https://www.mayoclinic.org/tests-procedures/robotic-surgery/about/pac- 20394974?p=1, downloaded from the internet on Jul. 12, 2018, 2 pp.
Notice of Acceptance for appl No. 2016343849, dated Aug. 5, 2021, 3 pages.
Notice of allowance for U.S. Appl. No. 15/948,369, dated Aug. 17, 2021, 10 pages.
Notice of allowance for U.S. Appl. No. 16/355,437, dated Oct. 28, 2021, 10 pages.
Office action for U.S. Appl. No. 15/948,351, dated Nov. 16, 2020, 10 pages.
Office action for U.S. Appl. No. 15/948,351, dated Sep. 29, 2021, 17 pages.
Office action for U.S. Appl. No. 16/865,904, dated Sep. 17, 2021, 13 pages.
Ramezanifard et al, 2007, A Novel Modeling Approach for Collision Avoidance in Robotic Surgery, 2007 Science Publications, American Journal of Applied Sciences 4(9):693-699, 7 pages.
International Preliminary Report on Patentability for PCT/US2016/059686 dated Feb. 17, 2017, 7 pages.
International Search Report for PCT/IB2020/057704 dated Feb. 18, 2021, 16 pages.
International Search Report for PCT/US2016/059686 dated Feb. 17, 2017, 4 pages.
Mayo Clinic, Robotic Surgery, https://www.mayoclinic.org/tests-procedures/robotic-surgery/about/pac- 20394974?p=1, downloaded from the internet on Jul. 12, 2018, 2 pgs.
Notice of Allowance for U.S. Appl. No. 15/948,369, dated Dec. 14, 2021, 11 pages.
PCT Invitation to Pay Additional Fees, PCT Application No. PCT/US2016/059686, Dec. 8, 2016, 2 pages.
U.S. Appl. No. 62/248,737, filed Oct. 30, 2015, Inventors: David P. Noonan et al., 76 pages.
Written Opinion of the International Search Authority for PCT/IB2020/057704 dated Feb. 18, 2021, 9 pages.
Written Opinion of the International Searching Authority for PCT/US2016/059686 dated Feb. 17, 2017, 6 pages.
Notice of Allowance for U.S. Appl. No. 15/948,351, dated Mar. 2, 2022, 10 pages.

ADVANCED BASKET DRIVE MODE

CROSS-REFERENCE TO RELATED APPLICATIONS

The present application claims priority to U.S. Provisional Patent Application Ser. No. 62/956,071, filed Dec. 31, 2019, entitled ADVANCED BASKET DRIVE MODE, the disclosure of which is hereby incorporated by reference in its entirety.

BACKGROUND

Field

The present disclosure relates to the field of medical devices and procedures and user interfaces.

Description of the Related Art

Various medical procedures involve the use of one or more devices configured to penetrate the human anatomy to reach a treatment site. Certain operational processes can involve inserting the one or more devices through the skin or an orifice of a patient to reach the treatment site and extract an object from the patient, such as a urinary stone.

SUMMARY

Described herein are one or more systems, devices, and/or methods to assist a physician or other in controlling a medical instrument to access to an object, such as a urinary stone, located within the human anatomy.

One general aspect includes a robotic system for performing a medical procedure, the robotic system including a robotic manipulator configured to: manipulate a medical instrument having a basket, the medical instrument configured to access a human anatomy; open the basket at a first opening speed and a second opening speed faster than the first opening speed; and close the basket at a first closing speed and a second closing speed faster than the first closing speed. The system can include an input device configured to receive one or more user interactions and initiate one or more actions by the robotic manipulator, the one or more actions may include at least one of directly controlled movement and pre-programmed motions. The system also can include control circuitry communicatively coupled to the input device and the robotic manipulator and configured to: in response to receiving a first user interaction via the input device, trigger a first pre-programmed motion of the robotic manipulator, the first pre-programmed motion including opening the basket at the second opening speed; and in response to receiving a second user interaction via the input device, trigger a second pre-programmed motion of the robotic manipulator, the second pre-programmed motion including closing the basket at the second closing speed. Other embodiments of this aspect include corresponding computer systems, apparatus, and computer programs recorded on one or more computer storage devices, each configured to perform the actions of the methods.

Implementations of the robotic system may include one or more of the following features. The robotic system may include a ureteroscope. The medical procedure may include ureteroscopy. The input device may include a control pad having directional controls configured to direct movement of the robotic manipulator along a plurality of axes and a plurality of buttons including a first button and a second button. The first user interaction may include double tapping the first button. The second user interaction may include double tapping the second button. The robotic system the control circuitry can be further configured to: in response to tapping the first button and the second button concurrently, trigger a third pre-programmed motion of the robotic manipulator including a repeated, short range, forward and backward movement at an accelerated speed. The control circuitry can be further configured to: in response to receiving a third user interaction, trigger a third pre-programmed motion of the robotic manipulator including a repeated, short range, forward and backward movement at an accelerated speed. The second pre-programmed motion may further include: detecting a torque on a drive mechanism of the basket; and in response to the torque exceeding a threshold, stopping the closing of the basket. The first user interaction and/or the second user interaction may include a voice command. Implementations of the described techniques may include hardware, a method or process, or computer software on a computer-accessible medium.

One general aspect includes a method for controlling a medical instrument using a robotic manipulator. The method can include manipulating, using the robotic manipulator, a medical instrument including a basket to access a human anatomy, the robotic manipulator configured to open the basket at a first opening speed and a second opening speed, the robotic manipulator further configured to close the basket at a first closing speed and a second closing speed; receiving, via an input device, one or more user interactions for triggering pre-programmed actions by the robotic manipulator. The method can further include, in response to receiving a first user interaction via the input device, triggering a first pre-programmed motion of the robotic manipulator, the first pre-programmed motion including opening the basket at the second opening speed, the second opening speed faster than the first opening speed. The method can further include, in response to receiving a second user interaction via the input device, triggering a second pre-programmed motion of the robotic manipulator, the second pre-programmed motion including closing the basket at the second closing speed, the second closing speed faster than the first closing speed. Other embodiments of this aspect include corresponding computer systems, apparatus, and computer programs recorded on one or more computer storage devices, each configured to perform the actions of the methods.

Implementations of the method may include one or more of the following features. The first user interaction may include double tapping a first button of the input device and second user interaction may include double tapping a second button of the input device. The method can further include, in response to tapping the first button and the second button concurrently, triggering a third pre-programmed motion of the robotic manipulator, the third pre-programmed motion including a repeated, short range, forward and backward movement at an accelerated speed. The method may further include, in response to receiving a movement input along a first axis on the input device, moving a central locus of the third pre-programmed motion of the robotic manipulator along the first axis; and repeating the short range, forward and backward movement at the central locus. The third pre-programmed motion may further include a repeated, rotational movement. The method may further include manipulating, using the robotic manipulator, an endoscope to access a human anatomy, the endoscope configured to capture images of the medical instrument within the human anatomy. The method may further include receiving, via an input device, a third user interaction for directly controlling movement of the medical instrument; and manipulating, using the robotic manipulator, the medical instrument along one or more axes of movement based on the received third user interaction. The second pre-programmed motion may further include: detecting a torque on a drive mechanism of the basket; and in response to the torque exceeding a threshold, stopping the closing of the basket. Implementations of the described techniques may include hardware, a method or process, or computer software on a computer-accessible medium.

One general aspect includes a control system for controlling a robotic device for performing a medical procedure. The control system can include an input device configured to receive one or more user interactions and initiate one or more actions by the robotic device, the one or more actions including at least one of directly-controlled movement and pre-programmed motions. The control system can further include a communication interface configured to send commands to the robotic device corresponding to the directly-controlled movement and the pre-programmed motions, the commands including: movement, by the robotic device, of a medical instrument having a basket, the medical instrument configured to access a human anatomy; opening the basket at a first opening speed and a second opening speed faster than the first opening speed; and closing the basket at a first closing speed and a second closing speed faster than the first closing speed. The control system can further include control circuitry communicatively coupled to the input device and the communication interface, the control circuitry configured to: in response to receiving a first user interaction, trigger a first pre-programmed motion of the robotic device, the first pre-programmed motion including opening the basket at the second opening speed; and in response to receiving a second user interaction, trigger a second pre-programmed motion of the robotic device, the second pre-programmed motion including closing the basket at the second closing speed. Other embodiments of this aspect include corresponding computer systems, apparatus, and computer programs recorded on one or more computer storage devices, each configured to perform the actions of the methods.

Implementations of the control system may include one or more of the following features. The input device may include directional controls configured to direct movement of the robotic device along a plurality of axes; and a plurality of buttons including a first button configured to trigger the first pre-programmed motion and a second button configured to trigger the second pre-programmed motion. Double-tapping the first button can trigger the first pre-programmed motion and double-tapping the second button can trigger the second pre-programmed motion. Single tapping the first button can trigger a third pre-programmed motion different from the first pre-programmed motion and single-tapping the second button can trigger a fourth pre-programmed motion different from the second pre-programmed motion. The control circuitry can be further configured to: in response to tapping the first button and the second button concurrently, trigger a third pre-programmed motion of the robotic device, the third pre-programmed motion including a repeated, short range, forward and backward movement at an accelerated speed. The control circuitry can be further configured to: in response to receiving, via the directional controls, a movement request along a first axis, move a central locus of the third pre-programmed motion of the robotic device along the first axis; and repeat the short range, forward and backward movement at the central locus. The input device may include a microphone configured to capture vocal user commands; and the control circuitry is further configured to identify a first vocal user command corresponding to the first user interaction, and a second vocal user command corresponding to the second user interaction. The robotic device may be located at a first geographic location different from a second geographic location of the control system; and the communication interface is further configured to send the commands over a wide area network. Implementations of the described techniques may include hardware, a method or process, or computer software on a computer-accessible medium.

One general aspect includes one or more non-transitory computer-readable media storing computer-executable instructions that, when executed by control circuitry, cause the control circuitry to perform operations including: manipulating, using a robotic device, a medical instrument having a basket to access a human anatomy, the robotic device configured to open the basket at a first opening speed and a second opening speed, the robotic device further configured to close the basket at a first closing speed and a second closing speed; receiving, via an input device, one or more inputs for triggering pre-programmed actions by the robotic device; in response to receiving a first input via the input device, triggering a first pre-programmed motion of the robotic device, the first pre-programmed motion including opening the basket at the second opening speed, the second opening speed faster than the first opening speed; and in response to receiving a second input via the input device, triggering a second pre-programmed motion of the robotic device, the second pre-programmed motion including closing the basket at the second closing speed, the second closing speed faster than the first closing speed. Other embodiments of this aspect include corresponding computer systems, apparatus, and computer programs recorded on one or more computer storage devices, each configured to perform the actions of the methods.

Implementations of the non-transitory computer-readable media may include one or more of the following features. The first input may include double tapping a first button of the input device and second input may include double tapping a second button of the input device. The computer-executable instructions can be further configured to cause the control circuitry to perform operations including: in response to tapping the first button and the second button concurrently, triggering a third pre-programmed motion of the robotic device, the third pre-programmed motion including a repeated, short range, forward and backward movement at an accelerated speed. The computer-executable instructions can be further configured to cause the control circuitry to perform operations may include: receiving, via the input device, a third input for controlling direct movement of the robotic device; and manipulating, using the robotic device, the medical instrument along one or more axes of movement based on the received third input. Implementations of the described techniques may include hardware, a method or process, or computer software on a computer-accessible medium.

For purposes of summarizing the disclosure, certain aspects, advantages and novel features have been described. It is to be understood that not necessarily all such advantages may be achieved in accordance with any particular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

Various embodiments are depicted in the accompanying drawings for illustrative purposes and should in no way be interpreted as limiting the scope of the disclosure. In addition, various features of different disclosed embodiments can be combined to form additional embodiments, which are part of this disclosure. Throughout the drawings, reference numbers may be reused to indicate correspondence between reference elements.

DETAILED DESCRIPTION

Figure 1:
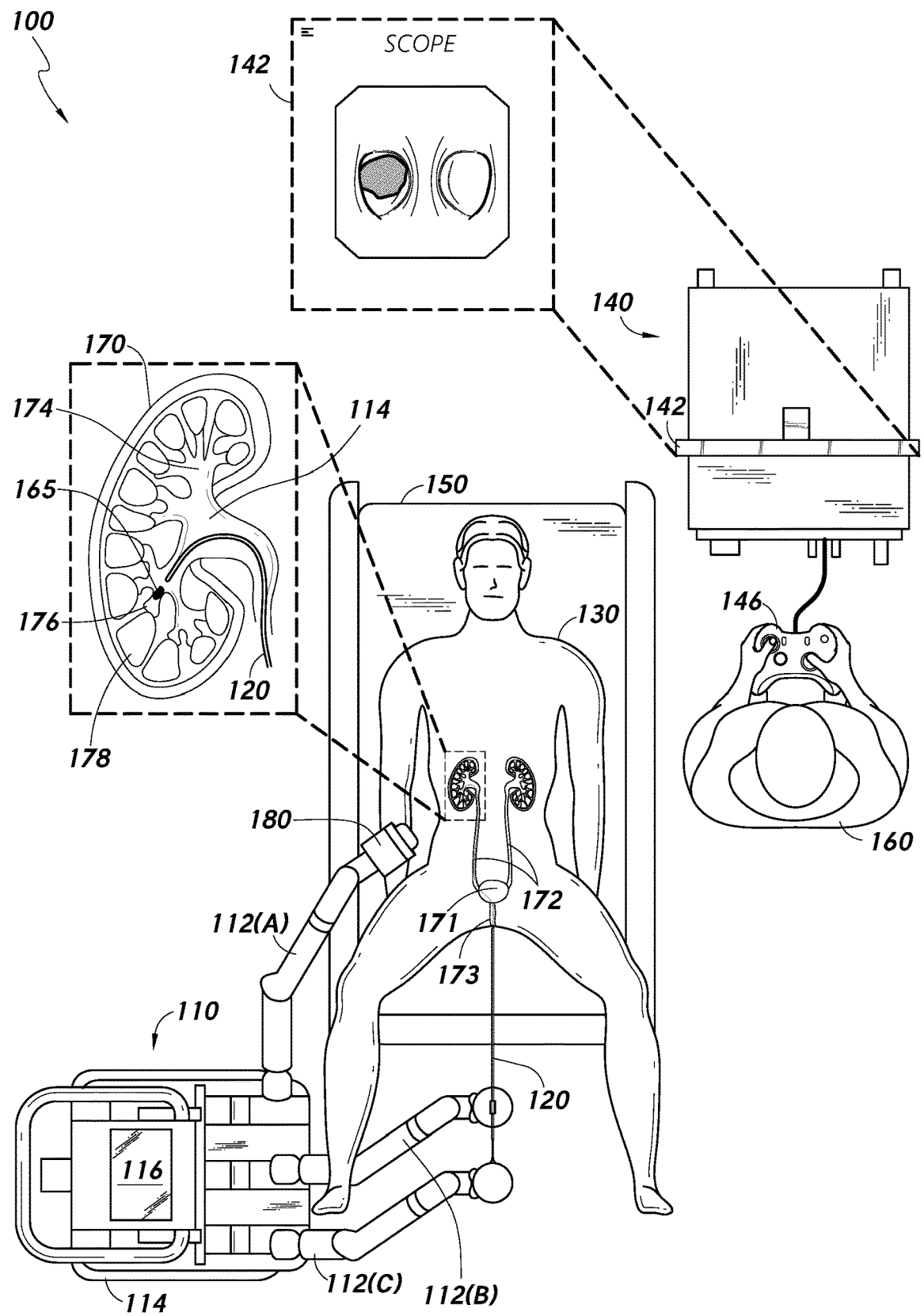
FIG. 1 illustrates an example medical system to perform or assist in performing medical procedures, according to certain embodiments.

The headings provided herein are for convenience only and do not necessarily affect the scope or meaning of disclosure. Although certain preferred embodiments and examples are disclosed below, the subject matter extends beyond the specifically disclosed embodiments to other alternative embodiments and/or uses and to modifications and equivalents thereof. Thus, the scope of the claims that may arise herefrom is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Certain standard anatomical terms of location may be used herein to refer to the anatomy of animals, and namely humans, with respect to the preferred embodiments. Although certain spatially relative terms, such as "outer," "inner," "upper," "lower," "below," "above," "vertical," "horizontal," "top," "bottom," and similar terms, are used herein to describe a spatial relationship of one device/element or anatomical structure to another device/element or anatomical structure, it is understood that these terms are used herein for ease of description to describe the positional relationship between element(s)/structures(s), as illustrated in the drawings. It should be understood that spatially relative terms are intended to encompass different orientations of the element(s)/structures(s), in use or operation, in addition to the orientations depicted in the drawings. For example, an element/structure described as "above" another element/structure may represent a position that is below or beside such other element/structure with respect to alternate orientations of the subject patient or element/structure, and vice-versa.

Overview

The present disclosure relates to techniques and systems for controlling a medical device such as a basket retrieval device for retrieving urinary stones. The basket retrieval device can be used in different situations during a medical procedure, such as ureteroscopy. For example, the basket can be used to capture a urinary stone, release the urinary stone, reposition the urinary stone, shake off the tissue on the basket, and/or break up urinary stone congestion. Different scenarios utilize different techniques for operating the basket retrieval device. The basket can be controlled to open/close, insert/retract, and/or rotate, with varying velocities depending on the scenario. In some embodiments, movement of the basket retrieval device is coordinated with movement of a scope for better feedback and control. Typically, the basket retrieval device is operated by two people, a physician controlling the insertion/retraction of the basket retrieval device and an assistant controlling opening/closing the basket itself. As such, cooperation and coordination between the physician and assistant is needed for successful operation of the device.

Kidney stone disease, also known as urolithiasis, is a relatively common medical condition that involves the formation, in the urinary tract, of a solid piece of material, referred to as "kidney stones," "urinary stones," "renal calculi," "renal lithiasis," or "nephrolithiasis." Urinary stones can be formed and/or found in the kidneys, the ureters, and the bladder (referred to as "bladder stones"). Such urinary stones form as a result of concentrated minerals and can cause significant abdominal pain once they reach a size sufficient to impede urine flow through the ureter or urethra. Urinary stones can be formed from calcium, magnesium, ammonia, uric acid, cysteine, and/or other compounds.

To remove urinary stones from the bladder and ureter, surgeons can insert a ureteroscope into the urinary tract through the urethra. Typically, a ureteroscope includes an endoscope at its distal end configured to enable visualization of the urinary tract. The ureteroscope can also include a lithotomy mechanism, such as the basket retrieval device, to capture or break apart urinary stones. As described above, during a ureteroscopy procedure, one physician/technician can control the position of the ureteroscope, while another other physician/technician can control the lithotomy mechanism.

In one example operation, the physician tries to capture the stone while the assistant controls opening/closing of the basket. This requires some amount of coordination as the physician inserts and articulates the basket (and possibly a scope at the same time), while the assistant needs to quickly close the basket around the urinary stone until the stone is fully captured. In another operation involving releasing the stone, the assistant needs to open the basket to the full amount and at high speed to release the stone. In an operation for shaking off the tissue, the assistant or physician needs to jiggle the basket back and forth at high frequency so that the tissue falls off from the basket. In an operation for repositioning the stone inside the basket, the assistant may need to slightly open the basket to give the stone the room for rotation, while the physician jiggles the basket retrieval device back and forth, and sometimes inserts or retracts the basket retrieval device at the same time to help adjust the basket position.

As described above, basket operation can have various levels of complexity, depending on the medical procedure. Conventional approaches employing a single, slow speed basket drive mode that require two users to operate do not provide the physician with sufficient flexibility or ease of use. Thus, there is a need for more advanced basket drive modes that allow physicians to unilaterally control the basket (e.g., adjusting basket velocity and/or opening/closing the basket) for more dynamic basket operation, as well as the ability to control multiple instruments at the same time.

In many embodiments, the techniques and systems are discussed in the context of a minimally invasive procedure. However, it should be understood that the techniques and systems can be implemented in the context of any medical procedure including, for example, percutaneous operations where access is gained to a target location by making a puncture and/or a minor incision into the body to insert a medical instrument, non-invasive procedures, therapeutic procedures, diagnostic procedures, non-percutaneous procedures, or other types of procedures. An endoscopic procedure can include a bronchoscopy, a ureteroscopy, a gastroscopy, nephroscopy, nephrolithotomy, and so on. Further, in many embodiments, the techniques and systems are discussed as being implemented as robotically-assisted procedures. However, it should also be appreciated that the techniques and systems can be implemented in other procedures, such as in fully-robotic medical procedures.

For ease of illustration and discussion, the techniques and systems are discussed in the context of removing urinary stones, such as kidneys stones from the kidneys. However, as noted above, the techniques and systems can be used to perform other procedures.

Medical System

FIG. 1 illustrates an example medical system 100 to perform or assist in performing medical procedures in accordance with one or more embodiments. Embodiments of the medical system 100 can be used for surgical and/or diagnostic procedures. The medical system 100 includes a robotic system 110 configured to engage with and/or control a medical instrument 120 to perform a procedure on a patient 130. The medical system 100 also includes a control system 140 configured to interface with the robotic system 110, provide information regarding the procedure, and/or perform a variety of other operations. For example, the control system 140 can include a display 142 to present a user interface 144 to assist the physician 160 in using the medical instrument 120. Further, the medical system 100 can include a table 150 configured to hold the patient 130 and/or an imaging sensor 180, such as a camera, x-ray, computed tomography (CT), magnetic resonance imaging (MRI), positron emission tomography (PET) device, or the like.

In some embodiments, the physician performs a minimally-invasive medical procedure, such as ureteroscopy. The physician 160 can interact with the control system 140 to control the robotic system 110 to navigate the medical instrument 120 (e.g., a basket retrieval device and/or scope) from the urethra up to the kidney 170 where the stone 165 is located. The control system 140 can provide information via a display 142 regarding the medical instrument 120 to assist the physician 160 in navigation, such as real-time images from the medical instrument 120 or the imaging sensor 180. Once at the site of the kidney stone, the medical instrument 120 can be used to break-up and/or capture a urinary stone 165.

In some implementations of using the medical system 100, a physician 160 can perform a percutaneous procedure. To illustrate, if the patient 130 has a kidney stone 165 in a kidney 170 that is too large to be removed through a urinary tract, the physician 160 can perform a procedure to remove the kidney stone through a percutaneous access point on the patient 130. For example, the physician 160 can interact with the control system 140 to control the robotic system 110 to navigate the medical instrument 120 (e.g., a scope) from the urethra up to the kidney 170 where the stone 165 is located. The control system 140 can provide information via a display 142 regarding the medical instrument 120 to assist the physician 160 in navigating the medical instrument 120, such as real-time images from the medical instrument 120 or the imaging sensor 180. Once at the site of the kidney stone, the medical instrument 120 can be used to designate a target location for a second medical instrument (not shown) to access the kidney percutaneously (e.g., a desired point to access the kidney). To minimize damage to the kidney, the physician 160 can designate a particular papilla as the target location for entering into the kidney with the second medical instrument. However, other target locations can be designated or determined. Once the second medical instrument has reached the target location, the physician 160 can use the second medical instrument and/or another medical instrument to extract the kidney stone from the patient 130, such as through the percutaneous access point. Although the above percutaneous procedure is discussed in the context of using the medical instrument 120, in some implementations a percutaneous procedure can be performed without the assistance of the medical instrument 120. Further, the medical system 100 can be used to perform a variety of other procedures.

In the example of FIG. 1, the medical instrument 120 is implemented as a basket retrieval device. Thus, for ease of discussion, the medical instrument 120 is also referred to as "the basket retrieval device 120." However, the medical instrument 120 can be implemented as various types of medical instruments including, for example, a scope (sometimes referred to as an "endoscope"), a needle, a catheter, a guidewire, a lithotripter, forceps, a vacuum, a scalpel, a combination of the above, or the like. In some embodiments, a medical instrument is a steerable device, while other embodiments a medical instrument is a non-steerable device. In some embodiments, a surgical tool refers to a device that is configured to puncture or to be inserted through the human anatomy, such as a needle, a scalpel, a guidewire, and so on. However, a surgical tool can refer to other types of medical instruments. In some embodiments, multiple medical instruments may be used. For example, an endoscope can be used with a basket retrieval device 120. In some embodiments, the medical instrument 120 may be a compound device incorporating several instruments, such as a vacuum, a basket retrieval device, a scope or various combinations of instruments.

The robotic system 110 can be configured to at least partly facilitate a medical procedure. The robotic system 110 can be arranged in a variety of ways depending on the particular procedure. The robotic system 110 can include one or more robotic arms 112 (robotic arms 112(a), 112(b), 112(c)) to engage with and/or control the medical instrument 120 to perform a procedure. As shown, each robotic arm 112 can include multiple arm segments coupled to joints, which can provide multiple degrees of movement. In the example of FIG. 1, the robotic system 110 is positioned proximate to the patient's 130 lower torso and the robotic arms 112 are actuated to engage with and position the medical instrument 120 for access into an access point, such as the urethra of the patient 130. With the robotic system 110 properly positioned, the medical instrument 120 can be inserted into the patient 130 robotically using the robotic arms 112, manually by the physician 160, or a combination thereof.

The robotic system 110 can also include a base 114 coupled to the one or more robotic arms 112. The base 114 can include a variety of subsystems, such as control electronics, a power source, pneumatics, an optical source, an actuator (e.g., motors to move the robotic arm), control circuitry, memory, and/or a communication interface. In some embodiments, the base 114 includes an input/output (I/O) device 116 configured to receive input, such as user input to control the robotic system 110, and provide output, such as patient status, medical instrument location, or the like. The I/O device 116 can include a controller, a mouse, a keyboard, a microphone, a touchpad, other input devices, or combinations of the above. The I/O device can include an output component, such as a speaker, a display, a haptic feedback device, other output devices, or combinations of the above. In some embodiments, the robotic system 110 is movable (e.g., the base 114 includes wheels) so that the robotic system 110 can be positioned in a location that is appropriate or desired for a procedure. In other embodiments, the robotic system 110 is a stationary system. Further, in some embodiments, the robotic system 110 is integrated into the table 150.

The robotic system 110 can be coupled to any component of the medical system 100, such as the control system 140, the table 150, the imaging sensor 180, and/or the medical instruments 120. In some embodiments, the robotic system is communicatively coupled to the control system 140. In one example, the robotic system 110 can receive a control signal from the control system 140 to perform an operation, such as to position a robotic arm 112 in a particular manner, manipulate a scope, and so on. In response, the robotic system 110 can control a component of the robotic system 110 to perform the operation. In another example, the robotic system 110 can receive an image from the scope depicting internal anatomy of the patient 130 and/or send the image to the control system 140 (which can then be displayed on the control system 140). Further, in some embodiments, the robotic system 110 is coupled to a component of the medical system 100, such as the control system 140, to receive data signals, power, and so on. Other devices, such as other medical instruments, intravenous bags, blood packs or the like can also be coupled to the robotic system 110 or other components of the medical system 100 depending on the medical procedure being performed.

The control system 140 can be configured to provide various functionality to assist in performing a medical procedure. In some embodiments, the control system 140 can be coupled to the robotic system 110 and operate in cooperation with the robotic system 110 to perform a medical procedure on the patient 130. For example, the control system 140 can communicate with the robotic system 110 via a wireless or wired connection (e.g., to control the robotic system 110, the basket retrieval device 120, receive an image(s) captured by a scope, etc.), control the flow of fluids through the robotic system 110 via one or more fluid channels, provide power to the robotic system 110 via one or more electrical connections, provide optical signals to the robotic system 110 via one or more optical fibers or other components, and so on. Further, in some embodiments, the control system 140 can communicate with a scope to receive sensor data. Moreover, in some embodiments, the control system 140 can communicate with the table 150 to position the table 150 in a particular orientation or otherwise control the table 150.

As shown in FIG. 1, the control system 140 includes various I/O devices configured to assist the physician 160 or others in performing a medical procedure. In some embodiments, the control system 140 includes an input device 146 that is employed by the physician 160 or another user to control the basket retrieval device 120. For example, the input device 146 can be used to navigate the basket retrieval device 120 within the patient 130. The physician 160 can provide input via the input device 146 and, in response, the control system 140 can send control signals to the robotic system 110 to manipulate the medical instrument 120.

Although the input device 146 is illustrated as a controller in the example of FIG. 1, the input device 146 can be implemented as a variety of types of I/O devices, such as a touchscreen/pad, a mouse, a keyboard, a microphone, a smart speaker, etc. As also shown in FIG. 1, the control system 140 can include the display 142 to provide various information regarding a procedure. For example, the control system 140 can receive real-time images that are captured by a scope and display the real-time images via the display 142. Additionally or alternatively, the control system 140 can receive signals (e.g., analog, digital, electrical, acoustic/sonic, pneumatic, tactile, hydraulic, etc.) a medical monitor and/or a sensor associated with the patient 130, and the display 142 can present information regarding the health of the patient 130 and/or an environment of the patient 130. Such information can include information that is displayed via a medical monitor including, for example, a heart rate (e.g., electrocardiogram (ECG), heart rate variability (HRV), etc.), blood pressure/rate, muscle bio-signals (e.g., electromyography (EMG)), body temperature, oxygen saturation (e.g., Spa)), carbon dioxide ($CO_2$), brainwave (e.g., electroencephalogram (EEG)), environmental temperature, and so on.

In some embodiments, the input device 146 is configured to directly control movement of the basket retrieval device 120, as well as trigger pre-programmed motions. In one embodiment, direct control involves movement that continues as long as an active input is provided by the user, for example, by pushing up or down on a joystick or actuating a button. Direct control can include movement along one or more axes, such as inserting/retracting, rotating clockwise/counterclockwise, moving left/right and/or moving up/down. Pre-programmed motions can include rapid open, rapid close, jiggle, or other pre-defined movements that are triggered by a command but do not require continuing input from the user. By using pre-programmed motions, operation of the basket retrieval device is simplified as complex movements can be initiated by simplified commands. For example, rather than requiring coordinated actions between the physician 160 and an assistant to close the basket over a stone, a rapid close action can be triggered by a single user using a simplified command (e.g., pressing or double-tapping a button).

In contrast to a regular speed opening of the basket, rapid open opens the basket at a faster speed. In some scenarios, rapid open can be used by the user to quickly open the basket to prepare for stone capture and can also be used to release the stone. In an embodiment, regular open is directly controlled by the user. For example, the drive mechanism of the basket may open the basket as long as a button is being pressed, but stops when the button is released or a torque threshold level is reached, which usually indicates the basket is fully open. This provides finer control over the basket mechanism. Meanwhile, in certain embodiments, rapid open is pre-programmed to complete a series of actions when triggered, with the drive mechanism engaging the basket to open until the threshold torque level is reached or a new command (e.g., a button press) is received. In combination, regular open and rapid open can provide the user with greater control and flexibility during a medical procedure, with regular open being used when finer control is needed and rapid open being used when speed and/or timing is more important.

In contrast to a regular speed closing of the basket, rapid close closes the basket at a faster speed. In some scenarios, rapid close can be used for the user to grasp the stone quickly and also close the basket quickly when it not being used. In an embodiment, regular close is directly controlled by the user. For example, the drive mechanism of the basket may close the basket as long as a button is being pressed, but stops when the button is released or a torque threshold level is reached, which usually indicates the basket is fully close or a stone is captured. This provides finer control over the basket mechanism. Meanwhile, in certain embodiments, rapid close is pre-programmed to complete a series of actions when triggered, with the drive mechanism engaging the basket to close until the threshold torque level is reached or a new command (e.g., a button press) is received. In combination, regular close and rapid close can provide the user with greater control and flexibility during a medical procedure, with regular close being used when finer control is needed and rapid close being used when speed and/or timing is more important.

In one embodiment, a jiggle motion of the basket retrieval device can be triggered by holding two buttons on the input device 146 at the same time. Other embodiments can trigger the jiggle motion with other button presses, touch screen selections, voice commands, and/or other user inputs. In some embodiments, the jiggle motion is a pre-programmed motion where the basket retrieval device inserts forward and retracts backward for a small fixed amount of basket travel at a higher speed compared to a normal basket insertion speed. For example, during direct control, the basket retrieval device can move (e.g., insert/retract) at a normal speed (1x speed), while during a pre-programmed motion, the basket retrieval device can move at an accelerated speed (e.g., 1.5x, 2x, 3x, or the like). This high frequency dynamic movement can be used to shake off tissue that attaches to the basket, shake off the stone during stone release, and/or can be used to break up stone congestion.

In some embodiments, the jiggle motion includes a variable movement. For example, the user can use a direct-control movement to move the basket retrieval device from a first location where it is performing a jiggle motion to a second location to continue performing the jiggle motion. In this scenario, the pre-programmed motion is combined with a direct-control movement. The variable jiggle motion can be used to adjust stone position to address the stone being stuck. In one embodiment, the variable jiggle motion is triggered by holding down a first button and a second button at the same time, while a joystick is moved to provide a direction of movement (e.g., insert/retract). While the user presses the first and second buttons, the basket jiggles back and forth for a fixed amount. If the user then uses the joystick to insert or retract while holding both buttons, the basket can move to a new position. When the user lets go of the insertion joystick, the basket will go back to the jiggle mode with the locus of its movement moved to the new position indicated by the user. With variable jiggle mode, the user can first jiggle to loosen or rotate the stone, then insert or retract to adjust the jiggle location based on, for example, visual feedback received from a scope or the imaging sensor 180, then continue the jiggle motion until the stone repositioned to the desired location.

FIG. 1 also shows various anatomy of the patient 130 relevant to certain aspects of the present disclosure. In particular, the patient 130 includes kidneys 170 fluidly connected to a bladder 171 via ureters 172, and a urethra 173 fluidly connected to the bladder 171. As shown in the enlarged depiction of the kidney 170, the kidney includes calyxes 174 (e.g., major and minor calyxes), renal papillae (including the renal papilla 176, also referred to as "the papilla 176"), and renal pyramids (including the renal pyramid 178). In these examples, a kidney stone 165 is located in proximity to the papilla 176. However, the kidney stone can be located at other locations within the kidney 170.

As shown in FIG. 1, to remove the kidney stone 165 in the example minimally-invasive procedure, the physician 160 can position the robotic system 110 at the foot of the table 150 to initiate delivery of the medical instrument 120 into the patient 130. In particular, the robotic system 110 can be positioned within proximity to a lower abdominal region of the patient 130 and aligned for direct linear access to the urethra 173 of the patient 130. From the foot of the table 150, the robotic arm 112(B) can be controlled to provide access to the urethra 173. In this example, the physician 160 inserts a medical instrument 120 at least partially into the urethra along this direct linear access path (sometimes referred to as "a virtual rail"). The medical instrument 120 can include a lumen configured to receive the scope and/or basket retrieval device, thereby assisting in insertion of those devices into the anatomy of the patient 130.

Once the robotic system 110 is properly positioned and/or the medical instrument 120 is inserted at least partially into the urethra 173, the scope can be inserted into the patient 130 robotically, manually, or a combination thereof. For example, the physician 160 can connect the medical instrument 120 to the robotic arm 112(C). The physician 160 can then interact with the control system 140, such as the input device 146, to navigate the medical instrument 120 within the patient 130. For example, the physician 160 can provide input via the input device 146 to control the robotic arm 112(C) to navigate the basket retrieval device 120 through the urethra 173, the bladder 171, the ureter 172, and up to the kidney 170.

The control system 140 can include various components (sometimes referred to as "subsystems") to facilitate its functionality. For example, the control system 140 can include a variety of subsystems, such as control electronics, a power source, pneumatics, an optical source, an actuator, control circuitry, memory, and/or a communication interface. In some embodiments, the control system 140 includes a computer-based control system that stores executable instructions, that when executed, implement various operations. In some embodiments, the control system 140 is movable, such as that shown in FIG. 1, while in other embodiments, the control system 140 is a stationary system. Although various functionality and components are discussed as being implemented by the control system 140, any of this functionality and/or components can be integrated into and/or performed by other systems and/or devices, such as the robotic system 110 and/or the table 150.

The medical system 100 can provide a variety of benefits, such as providing guidance to assist a physician in performing a procedure (e.g., instrument tracking, patient status, etc.), enabling a physician to perform a procedure from an ergonomic position without the need for awkward arm motions and/or positions, enabling a single physician to perform a procedure with one or more medical instruments, avoiding radiation exposure (e.g., associated with fluoroscopy techniques), enabling a procedure to be performed in a single-operative setting, providing continuous suction to remove an object more efficiently (e.g., to remove a kidney stone), and so on. Further, the medical system 100 can provide non-radiation-based navigational and/or localization techniques to reduce physician exposure to radiation and/or reduce the amount of equipment in an operating room. Moreover, the medical system 100 can divide functionality into the control system 140 and the robotic system 110, each of which can be independently movable. Such division of functionality and/or movability can enable the control system 140 and/or the robotic system 110 to be placed at locations that are optimal for a particular medical procedure, which can maximize working area around the patient, and/or provide an optimized location for a physician to perform a procedure. For example, many aspects of the procedure can be performed by the robotic system 110 (which is positioned relatively close to the patient) while the physician manages the procedure from the comfort of the control system 140 (which can be positioned farther way).

In some embodiments, the control system 140 can function even if located in a different geographic location from the robotic system 110. For example, in a tele-health implementation, the control system 140 is configured to communicate over a wide area network with the robotic system 110. In one scenario, a physician 160 may be located in one hospital with the control system 140 while the robotic system 110 is located in a different hospital. The physician may then perform the medical procedure remotely. This can be beneficial where remote hospitals, such as those in rural areas, have limited expertise in particular procedures. Those hospitals can then rely on more experienced physicians in other locations. In some embodiments, a control system 140 is able to pair with a variety of robotic systems 110, for example, by selecting a specific robotic system and forming a secure network connection (e.g., using passwords, encryption, authentication tokens, etc.). Thus, a physician in one location may be able to perform medical procedures in a variety of different locations by setting up a connection with robotic systems 110 located at each of those different locations.

In some embodiments, the robotic system 110, the table 150, the medical instrument 120, the needle and/or the imaging sensor 180 are communicatively coupled to each other over a network, which can include a wireless and/or wired network. Example networks include one or more personal area networks (PANs), one or more local area networks (LANs), one or more wide area networks (WANs), one or more Internet area networks (IANs), one or more cellular networks, the Internet, etc. Further, in some embodiments, the control system 140, the robotic system 110, the table 150, the medical instrument 120, and/or the imaging sensor 180 are connected for communication, fluid/gas exchange, power exchange, and so on via one or more support cables.

Although not illustrated in FIG. 1, in some embodiments the medical system 100 includes and/or is associated with a medical monitor configured to monitor health of the patient 130 and/or an environment in which the patient 130 is located. For example, a medical monitor can be located in the same environment where the medical system 100 is located, such as within an operating room. The medical monitor can be physically and/or electrically coupled to one or more sensors that are configured to detect or determine one or more physical, physiological, chemical, and/or biological signals, parameters, properties, states and/or conditions associated with the patient 130 and/or the environment. For example, the one or more sensors can be configured to determine/detect any type of physical properties, including temperature, pressure, vibration, haptic/tactile features, sound, optical levels or characteristics, load or weight, flow rate (e.g., of target gases and/or liquid), amplitude, phase, and/or orientation of magnetic and electronic fields, constituent concentrations relating to substances in gaseous, liquid, or solid form, and/or the like. The one or more sensors can provide the sensor data to the medical monitor and the medical monitor can present information regarding the health of the patient 130 and/or the environment of the patient 130. Such information can include information that is displayed via a medical monitor including, for example, a heart rate (e.g., EGG, HRV, etc.), blood pressure/rate, muscle bio-signals (e.g., EMG), body temperature, oxygen saturation (e.g., $SpO_2$), $CO_2$, brainwave (e.g., EEG), environmental temperature, and so on. In some embodiments, the medical monitor and/or the one or more sensors are coupled to the control system 140 and the control system 140 is configured to provide information regarding the health of the patient 130 and/or the environment of the patient 130.

Example Controller

Figure 2A:
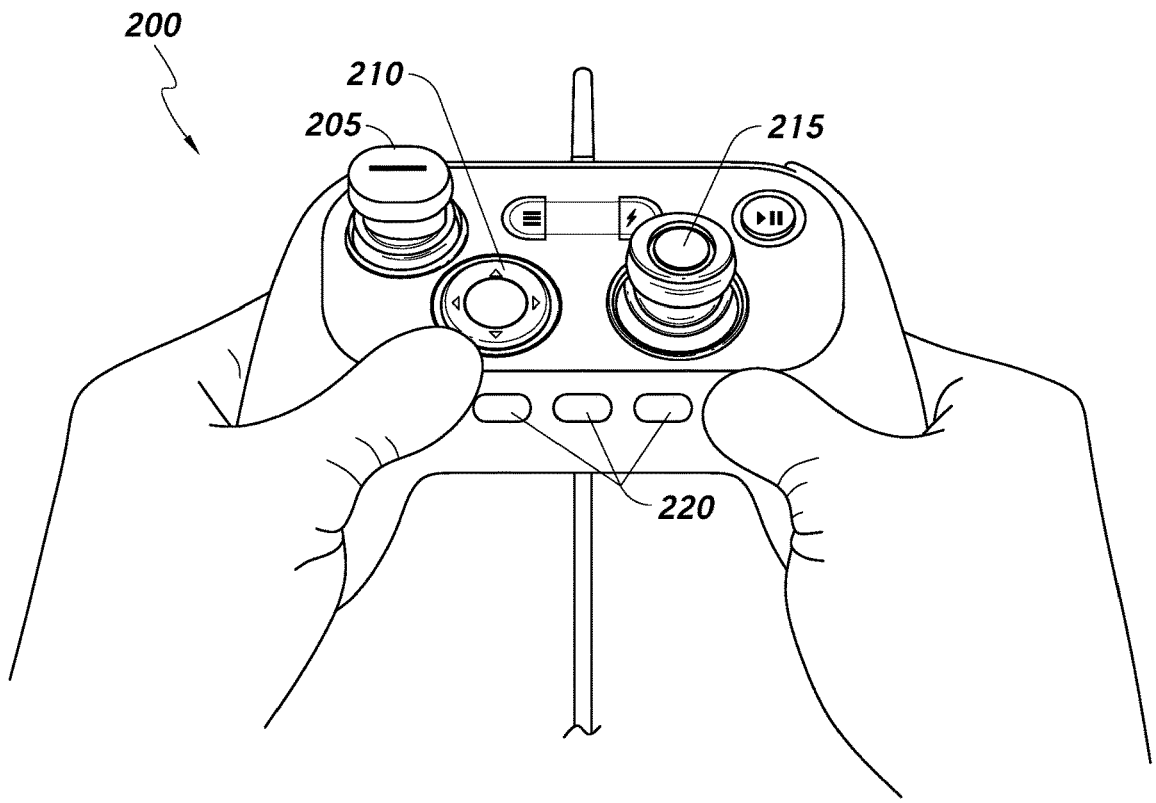
FIGS. 2A-2B illustrates a perspective view and a top profile view of a controller, respectively, for the medical system, according to certain embodiments.
Figure 2B:
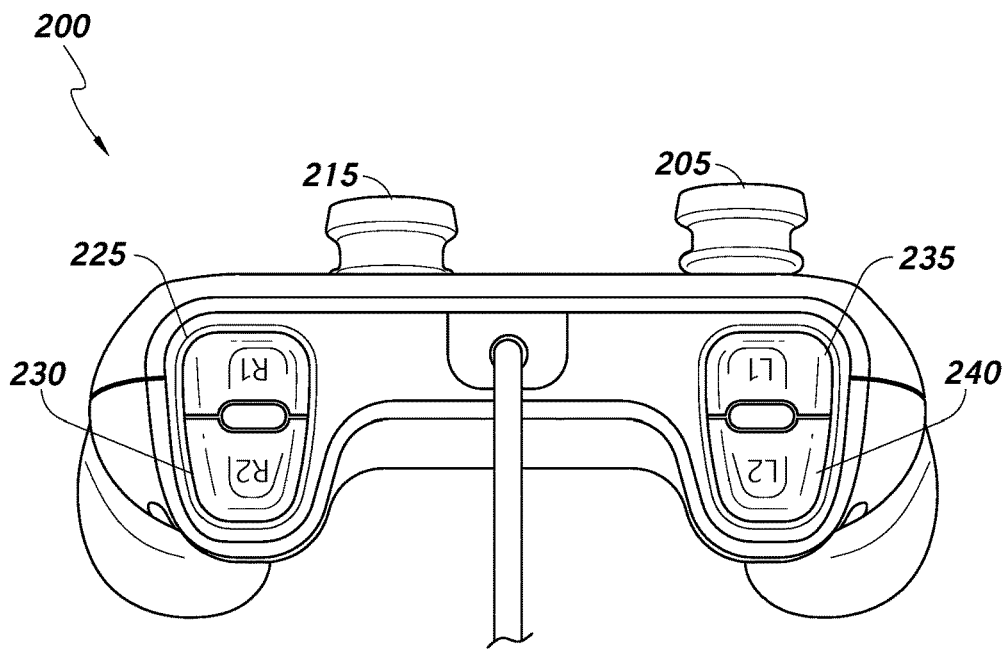

FIG. 2A and FIG. 2B illustrates a perspective view and a top profile view of a controller 200 for the control system 140, respectively, according to certain embodiments. As described in FIG. 1, the input device 146, in some embodiments, is a controller 200 or includes a controller 200. The face of the controller can include axis movement inputs, such one or more joysticks 205, 215 and one or more directional pads 210. In some embodiments, the joysticks 205, 215 provide analog input while the directional pad 210 provides digital input. The face of the controller can further include a plurality of buttons 220 to provide additional controls. In the example illustrated in FIG. 2B, the controller 200 includes four buttons on the top side of the controller: R1 225, R2 230 L1 235, and L2 240. Other embodiments can include a different number of buttons and/or a different layout. In some embodiments, the controller 200 may be a game console controller repurposed to work with the robotic system 110. For example, the controller game firmware may be overwritten with a medical device firmware and/or an input device manager may be installed in a component of the medical system 100 (e.g., the control system 140) to convert inputs from the controller into inputs understandable by the robotic system 110.

In one embodiment, rapid open can be triggered by double tapping the pendant top lower right button (R2 225) and rapid close can be triggered by double tapping the pendant top lower left button (L2 240). Users can double tap to rapidly open the basket, and double tap to rapidly close the basket. Double tap operation provides the user with easy access to the pre-programmed commands using the top two buttons (R2, L2). Meanwhile, the other inputs on the controller can be used for other functions, including controlling other medical instruments, such as inserting the scope, articulating the scope, and/or inserting the basket. These other functions can be triggered at the same time or independent from the pre-programmed motions. As will be apparent, other embodiments can configure the controller in different ways. For example, rapid open/rapid close can be triggered using other buttons and/or other interactions (e.g., using single tap, double tap, holding down a button, etc.). In one embodiment, the button mappings are switched, with rapid open triggered by the L2 button and rapid close triggered by the R2 button 225.

In one embodiment, jiggle motion of the basket retrieval device can be triggered by holding both the top lower right button (R2 225) and the top lower left button (L2 24) at the same time. By requiring both buttons to be pressed, the buttons used for rapid open and rapid close (R2/L2) can be dual-purpose, allowing more commands to be mapped to the controller 200 inputs. In one embodiment, the R2 and L2 buttons are triple-purpose, with single taps of the R2 and L2 buttons, respectively, each triggering another action. For example, single tapping R2 may initiate regular speed open of the basket while single tapping L2 may initiate regular speed close of the basket or vice versa. Other embodiments can trigger the jiggle motion with other button presses.

As described in FIG. 1, the jiggle motion can include a variable movement. In one embodiment, the first joystick 205 may be configured to directly control insertion and retraction movement of the basket retrieval device 120. While holding down R2 and L2 to trigger the jiggle motion, the user can move the joystick 205 up to further insert the basket retrieval device 120 to a new location in the patient's body. Alternatively, the user can move the joystick 205 down to retract the basket retrieval device 120 to a new location towards the entry point into the body. Once the user releases the joystick 205 (while still holding down R2 and L2), the jiggle motion can continue with the locus at the new location. As will be apparent, insertion and retraction can be mapped to other controller inputs, such the second joystick 215 or the directional pad 210.

Controller 200 operation can be customizable in some embodiments. The control system 140 can include a user interface that allows assigning of pre-programmed motions (e.g., rapid open/close, jiggle, etc.) to a desired controller layout by the user. For example, the user can assign rapid open or rapid close to any of the top buttons 220, the directional pad 210 or one of the joysticks 205, 215.

In some embodiments, triggering the pre-programmed motions can be at least partially automated. Machine learning or computer vision algorithms can be implemented to recognize when the basket retrieval device 120 is in the right position to perform a pre-programmed motion. For example, the medical system 100, using its imaging sensor 180, scope, or other sensing device can recognize that the basket is sufficiently near to the urinary stone 165 that rapid open can be triggered to capture the device. Once a threshold distance is reached, rapid open can be triggered to rapidly open the basket. Additional pre-programmed motions can also be chained together with the rapid open. For example, after opening the basket, a pre-programmed motion to further insert the basket retrieval device 120 such that the urinary stone is surrounded by the basket ("forward insertion" pre-programmed motion) can be triggered. Next, a rapid close could then be automatically triggered to capture the urinary stone 165.

As a safety precaution, pre-programmed motions can be configured to only automatically trigger in a specific mode ("auto-capture" mode) where automated motions are allowed. This auto-capture mode could be enabled using one of the buttons or other inputs on the controller 200 or via a menu setting in the control system 140 interface. In one scenario, the physician 160 moves the basket retrieval device 120 to the correct location near the urinary stone 165 using directly-controlled movement. The physician can then enable the auto-capture mode. If the stone is sufficiently close to meet or exceed a distance threshold, the auto-capture pre-programmed motions (e.g., rapid open, forward insertion, and/or rapid close) is automatically triggered. If the distance is greater than the distance threshold, the physician can further adjust the location of the basket retrieval device 120 until the auto-capture pre-programmed motions are triggered.

While FIGS. 2A-2B have illustrated one embodiment of a controller 200, other types of controllers or other input devices can also be used with the control system 140. For example, the input device 146 for the controls system 140 can be wireless (e.g., Wi-Fi, Bluetooth, etc.) or wired (e.g., universal serial bus (USB)). In another example, the input device 146 can be a graphical user interface (GUI) implemented on a touch screen device, such as a tablet or smart phone. In one example, the controller can be a smart speaker with a built-in microphone that accepts voice commands. In another example, the input device 146 may be controllers for a virtual reality or augmented reality system.

Urinary Stone Capture

Figure 3A:
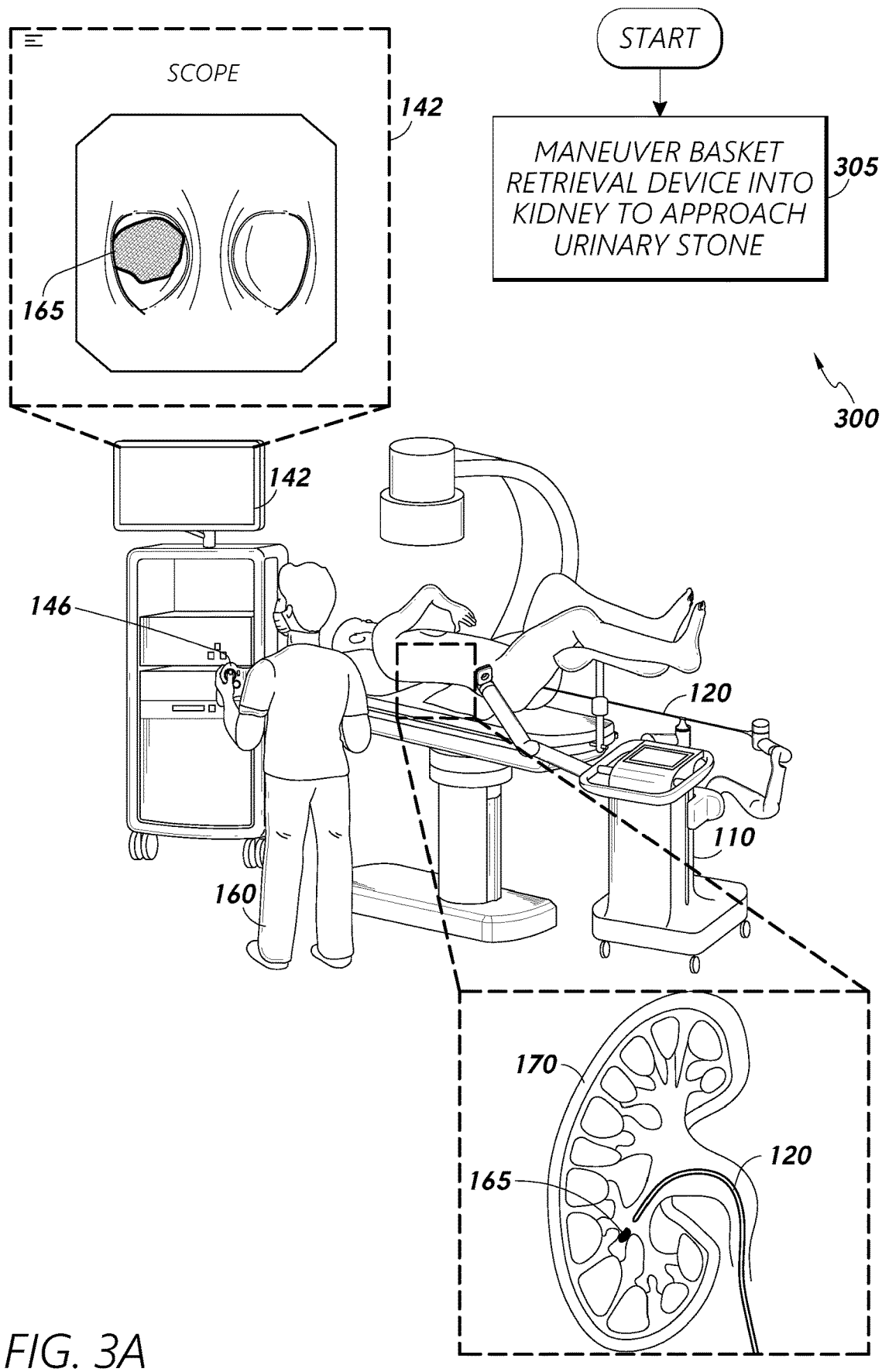
FIGS. 3A-3C illustrate a urinary stone capture procedure, according to certain embodiments.
Figure 3B:
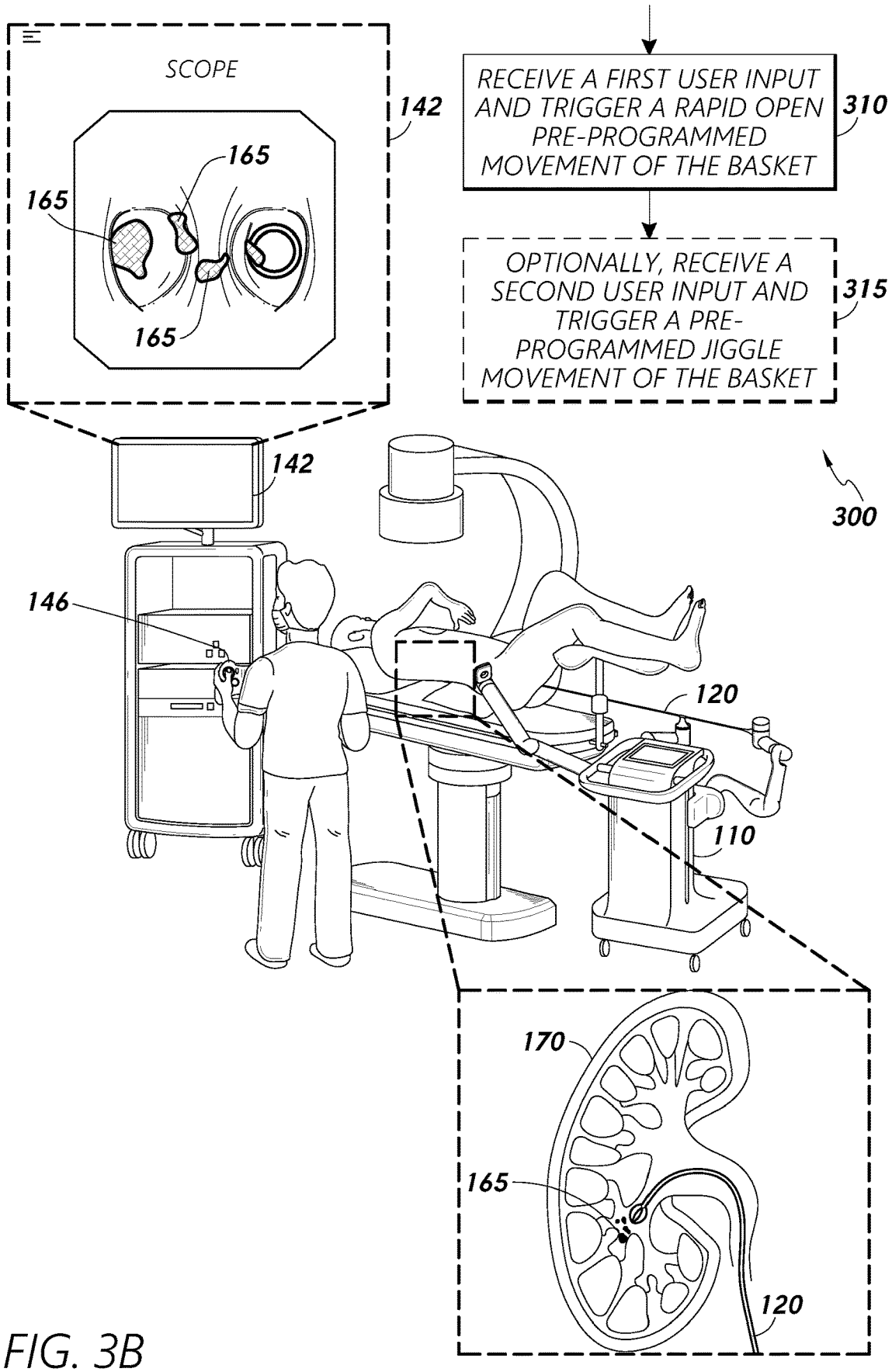
Figure 3C:
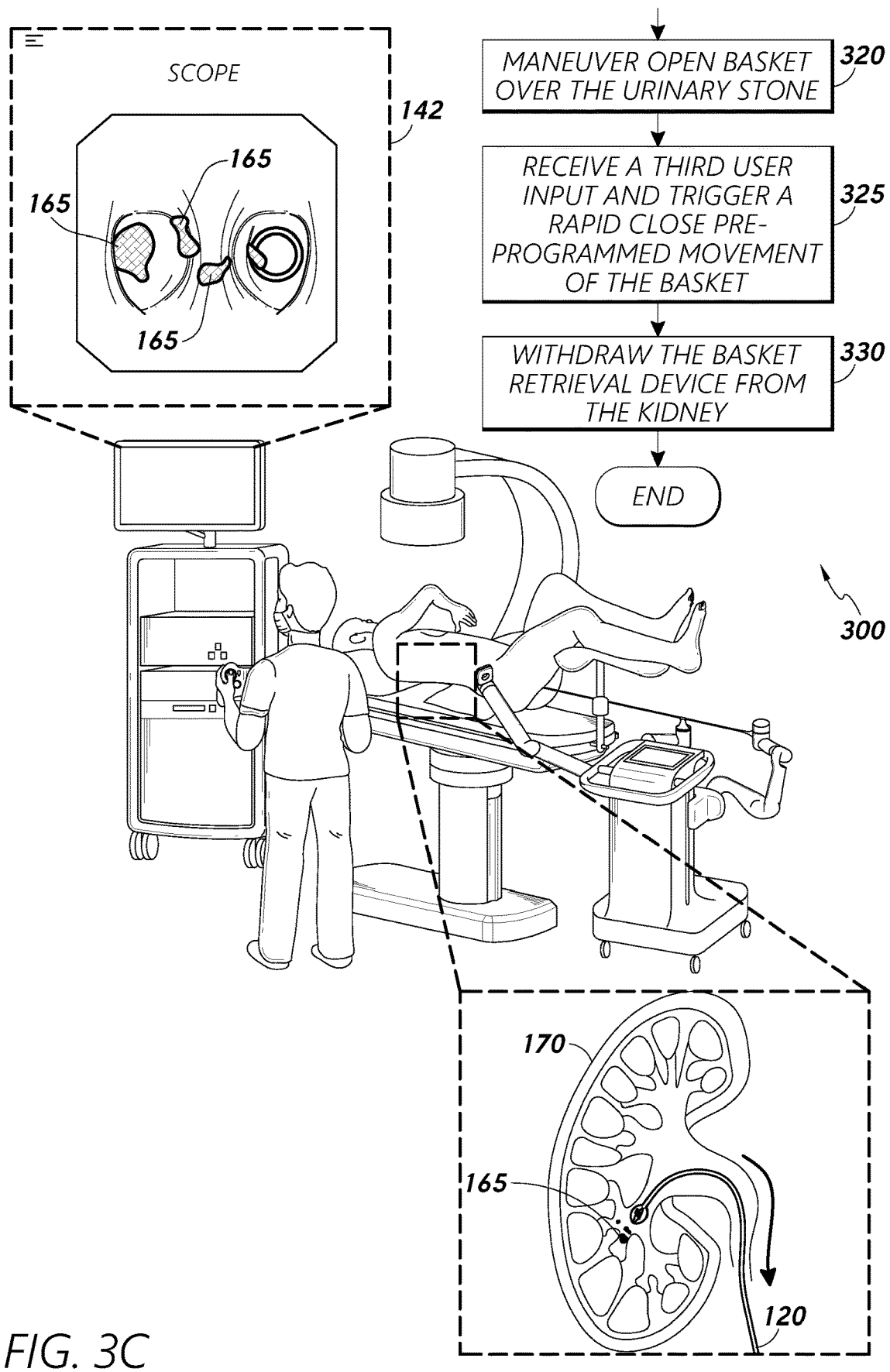

FIGS. 3A-3C illustrate a urinary stone capture procedure, according to certain embodiments. In these examples, the medical system 100 is arranged in an operating room to remove a kidney stone from the patient 130. In many instances of such a procedure, the patient 130 is positioned in a modified supine position with the patient 130 slightly tilted to the side to access the posterior or side of the patient 130. The urinary stone capture procedure may also be performed with the patient in a regular supine position, as show in in FIG. 1. Although FIGS. 3A-3C illustrate use of the medical system 100 to perform a minimally-invasive procedure to remove a kidney stone from the patient 130, the medical system 100 can be used to remove a kidney stone in other manners and/or to perform other procedures. Further, the patient 130 can be arranged in other positions as desired for a procedure. Various acts are described in FIGS. 3A-3C and throughout this disclosure as being performed by the physician 160. It should be understood that these acts can be performed directly by the physician 160, indirectly by the physician with the aid of the medical system 100, by a user under direction of the physician, by another user (e.g., a technician), and/or any other user.

Although particular robotic arms of the robotic system 110 are illustrated as performing particular functions in the context of FIGS. 3A-3C, any of the robotic arms 112 can be used to perform the functions. Further, any additional robotic arms and/or systems can be used to perform the procedure. Moreover, the robotic system 110 can be used to perform other parts of the procedure.

At block 305, the basket retrieval device 120 is maneuvered into the kidney 170 to approach the urinary stone 165. In some scenarios, the physician 160 or other user uses the input device 146 to directly control movement of the basket retrieval device 120. Such directly controlled movement can include insertion/retraction, flexing the basket retrieval device 120 left or right, rotation, and/or regular open/close of the basket. Using various movements, the basket retrieval device 120 is placed close to the stone.

At block 310, the rapid open pre-programmed movement is triggered in response to a user input (e.g., double-tapping a button). Rapid open causes the basket of the basket retrieval device 120 to open at an accelerated rate. Using rapid open allows the basket retrieval device 120 to more quickly get into position to capture the urinary stone 165, reducing the chances that extraneous movement (e.g., by the basket retrieval device or due to respiration/circulatory/urine flow movements within the kidney) moves the basket retrieval device 120 out of position. The rapid open movement can be triggered by double tapping a controller 200 button, using different inputs on the controller, or by using another type of input device, such as a voice command.

In some embodiments, a laser, shock wave device, or other device is used to break up the stone. The laser or other device may be incorporated into the basket retrieval device 120 or may be a separate medical instrument. The device for breaking up the stone may also controlled by the same input device (e.g., controller 200) as for triggering rapid open, rapid close and/or the jiggle motion. In some situations, the stone 165 is small enough that breaking up the stone into smaller pieces is not needed. In those cases, block 315 can be skipped and the process can proceed to block 320.

Optionally, at block 315, the pre-programmed jiggle motion is triggered to aid in clearing stone congestion or otherwise move the stone(s). For example, if the urinary stone 165 is broken into smaller pieces as discussed above, the jiggle motion can be used to separate the stones apart. The jiggle motion can be a pre-programmed motion where the basket retrieval device inserts forward and retracts backward for a small fixed amount of basket travel at a higher speed compared to a normal basket insertion speed. The pre-programmed jiggle motion can be triggered by pressing two buttons of the controller 200 simultaneously, using a different inputs on the controller, or by using another type of input device, such as a voice command.

At block 320, the open basket is maneuvered to surround the urinary stone 165 or a smaller piece of the urinary stone. In some scenarios, maneuvering is accomplished by directly-controlled movement by the physician 160 of the basket retrieval device 120. In some embodiments, a forward insertion pre-programmed motion can be used to surround the stone with the basket. For example, if the basket is formed by wires, the forward insertion movement can include a forward movement with, optionally, a slight sideways offset to one side to avoid hitting the stone with the wires forming the distal end of the basket. Once the stone has passed the distal end, an optional sideways motion opposite the first sideways offset motion can be applied to the basket to center the basket around the stone. In other embodiments, such as with a basket formed by plurality of tines, insertion of the basket is coordinated with closing the tines in order to center the basket longitudinally around the stone and avoid moving the stone during basket closure.

The forward insertion movement can be triggered by using inputs on the controller 200 or by using another type of input device, such as a voice command. While the above has described a pre-programmed forward insertion movement, this movement can also be accomplished by the user using directly controlled movement to surround the urinary stone.

At block 325, the rapid close programmed movement is triggered in response to a user input (e.g., double-tapping a button). Rapid close causes the basket of the basket retrieval device 120 to close at an accelerated rate. The closing motion can continue until the basket fully closes and/or a threshold torque is reached. When the drive mechanism of the basket reaches the torque threshold, that can indicate that the basket has closed over the stone, which is preventing further closing of the basket. Limiting the torque can protect the basket from any damage due to increased stress/force applied during closure. Using rapid close allows the basket retrieval device 120 to more quickly capture the urinary stone 165, reducing the chances that extraneous movement (e.g., by the patient or the basket retrieval device 120) moves the basket retrieval device 120 out of position. The rapid close movement can be triggered by double tapping a controller 200 button, using different inputs on the controller, or by using another type of input device, such as a voice command. Optionally, the jiggle motion can be triggered to help adjust the stone 165 position for easier withdrawal of the stone from the kidney.

At block 330, the basket retrieval device 120 is withdrawn from the kidney 170 and then out of the patient's body. The rapid open movement can optionally be triggered once the basket retrieval device 120 is outside the patient's body in order to quickly release the captured stone.

If additional stones (or large pieces of a broken-up stone 165) exist, the basket retrieval device 120 may be reinserted into the patient to capture the remaining large pieces. In some embodiments, a vacuum instrument can be used to facilitate removal of the pieces. In some situations, the stone pieces may be sufficiently small that they can be passed by the patient naturally.

Example Basket Retrieval Device

Figure 4A:
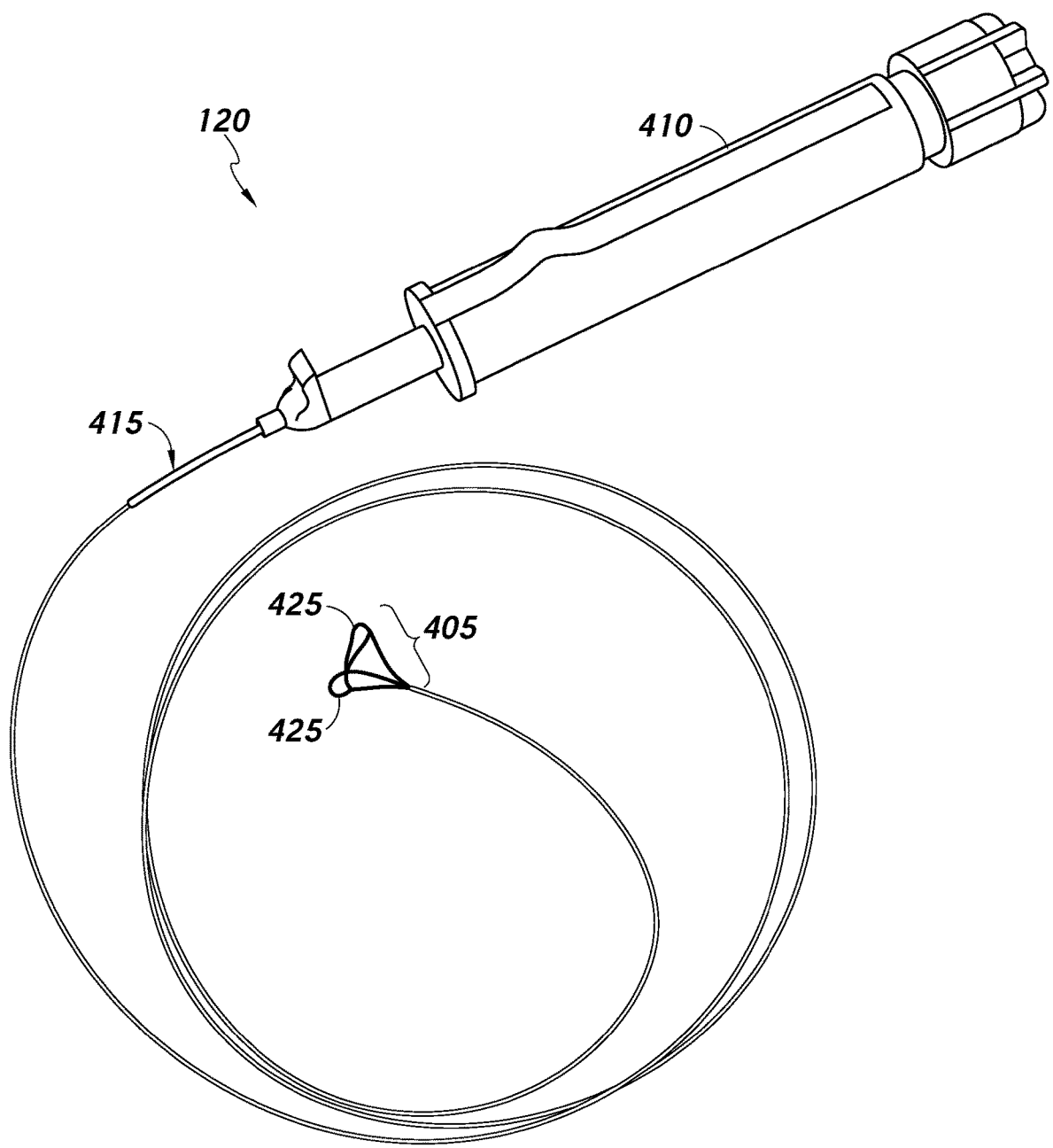
FIGS. 4A-4B illustrates a basket retrieval device and several basket configurations, respectively, according to certain embodiments.
Figure 4B:
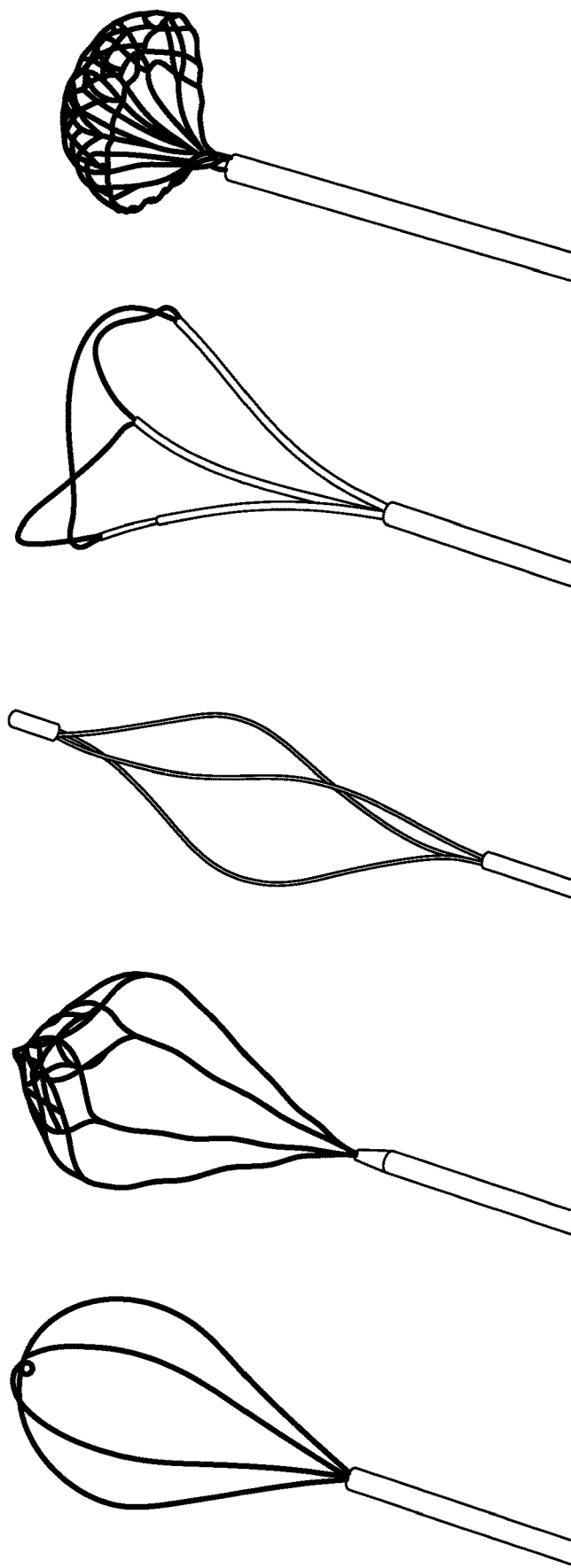

FIG. 4A illustrates a basket retrieval device 120, according to certain embodiments. The basket retrieval device 120 can include a basket 405 formed on the distal side, a handle 410 on the proximal side, a sheath 415 between the basket and the handle, and a basket drive mechanism 420. The basket can be formed in a variety of ways to capture urinary stones. In some embodiments, the basket is formed by two or more wire loops 425 that expand to form a space into which a stone is maneuvered and contract around the stone to capture it. As shown in FIG. 4B, the wires can be configured to form various shapes, such as a bulb, teardrop, helical, bowl shape or the like. In other embodiments, the basket is formed by two substantially oval or round bowls with recesses facing each other to form a hollow area for the urinary stone. In some embodiments, the basket is formed by a plurality of tines configured to close around a stone. The basket can be made from a variety of materials, such as nitinol, nickel, titanium, steel, cobalt-chrome alloy, other types of metals, ceramics, polymers such as plastic, or combinations of the same.

The handle 410 of the basket retrieval device 120 can be operated by a user or a robot. In some embodiments, the basket drive mechanism 420 is built into the handle. Engaging the drive, for example, with a sliding or twisting motion, can cause the basket to open or close. In one embodiment, engaging the drive to the open position causes basket wires to extend out of the sheath into an open basket position. Engaging the drive to the closed position can cause the basket wires to retract towards the sheath, collapsing the basket. If a urinary stone is inside the basket, the stone is captured by the closing of the basket wires.

A scope (not shown), which may be part of the basket retrieval device 120 or used in conjunction with it, can be configured to navigate within the human anatomy, such as within a natural orifice or lumen of the human anatomy. For example, the scope can include a channel through which the distal portion of the basket retrieval device 120 can be inserted. A scope can include, for example, a ureteroscope (e.g., for accessing the urinary tract), a laparoscope, a nephroscope (e.g., for accessing the kidneys), a bronchoscope (e.g., for accessing an airway, such as the bronchus), a colonoscope (e.g., for accessing the colon), an arthroscope (e.g., for accessing a joint), a cystoscope (e.g., for accessing the bladder), and so on. A scope can also be articulable, such as a distal portion of the scope, so that the scope can be steered within the human anatomy. A scope can include telescoping parts, such as an inner leader portion and an outer sheath portion, which can be manipulated to telescopically extend the scope. In some embodiments, a scope includes a working channel for deploying medical instruments (e.g., lithotripters, basketing devices, forceps, etc.), irrigation, and/or aspiration to an operative region at a distal end of the scope. A scope can accommodate wires and/or optical fibers to transfer signals to/from an optical assembly and a distal end of the scope, which can include an imaging device, such as an optical camera. A scope can also accommodate optical fibers to carry light from approximately-located light sources, such as light-emitting diodes, to the distal end of the scope. The distal end of a scope can also include an opening for a working channel to deliver tools, irrigation, and/or aspiration to an operative site. The distal end of a scope can also include a port for an imaging device, such as a camera, that can be configured to capture images of an internal anatomical space. The distal end of a scope can include ports for light sources to illuminate an anatomical space when using an imaging device. In some embodiments, the scope is configured to be controlled by the robotic system 110. The scope can include components to engage with the robotic system 110.

Example Pre-Programmed Movements

Figure 5:
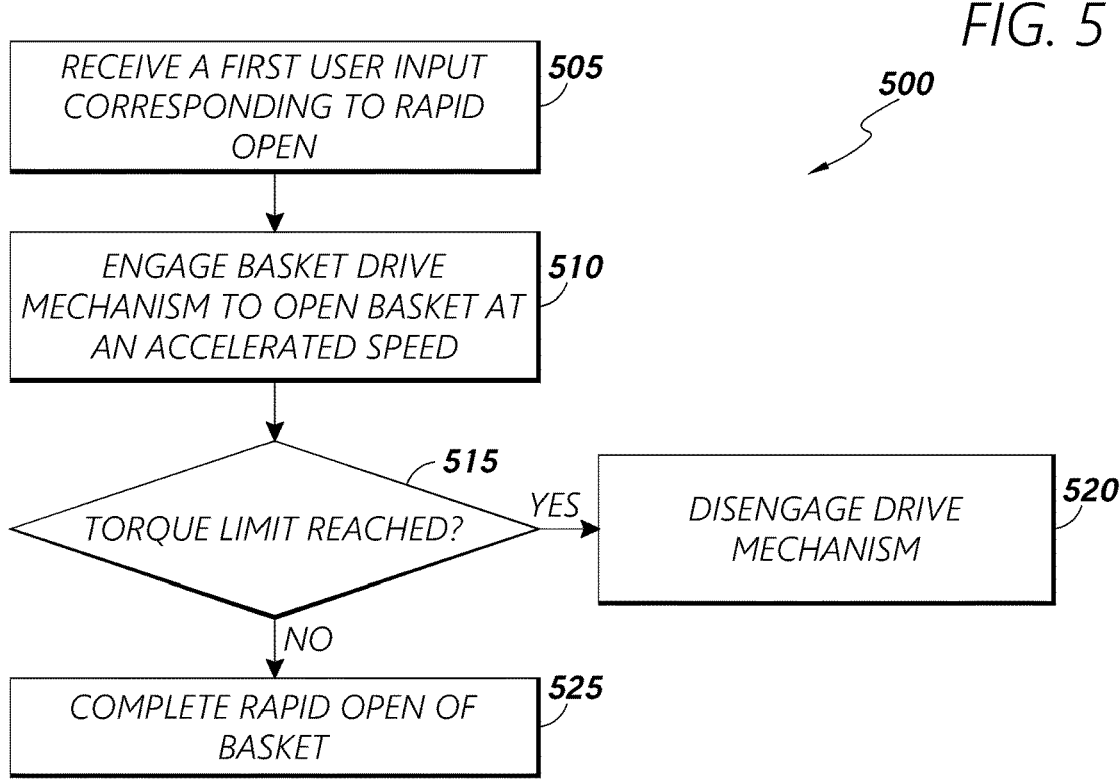
FIG. 5 is a flow diagram of a pre-programed rapid open process, according to certain embodiments.

FIG. 5 is a flow diagram of a pre-programed rapid open process 500, according to certain embodiments. The rapid open process 500 can be performed by the robotic system 110 or by another component of the medical system 100 of FIG. 1. For example, the robotic system 110 may be manipulating a basket retrieval device 120 with one or more of its arms. The process 500 may be performed according to the inputs provided by a user (e.g., physician) or may at least be partially automated. While the following describes one possible sequence to the process, other embodiments can perform the process in a different order.

At block 505, a control system 140 of the robotic system 110 receives a first user input from an input device 146. For example, the input may be double-tapping a button, a voice command, or other input. In one embodiment, the first input is double-tapping a first button on the controller 200 of FIGS. 2A-2B.

At block 510, the robotic system 110 engages the basket drive mechanism to open the basket 405 of the basket retrieval device 120 at an accelerated speed. In some embodiments, the basket drive mechanism 420 is configured to operate in at least two speeds: a first speed corresponding to a regular opening speed of the basket, and a second speed faster than the first speed. In one embodiment, the regular opening speed is used when the basket is opened using directly controlled movement rather than a pre-programmed motion.

At block 515, a torque sensor, which may be located in the basket retrieval device 120 or the robotic arm 112, determines the torque being applied by the basket drive mechanism 420 to the basket 405. If the torque meets or exceeds a torque limit configured for the robotic system 110, then the drive mechanism is disengaged. For example, the torque limit may be reached if there is tissue preventing the basket from opening. If the torque limit is reached, then the process 500 proceeds to block 520. Otherwise, the process 500 proceeds to block 525.

At block 520, the torque limit is reached and the drive mechanism is disengaged. As something is preventing the basket from further opening, additional movement could damage the basket 405 or surrounding tissue.

At block 525, the rapid open movement is completed. The basket 405 may be fully open (e.g., as indicated by the drive mechanism torque) or have otherwise reached the desired open configuration. For example, the rapid open movement may be configured to stop at 50%, 60%, 70%, 80%, 90%, 100%, or other amount of the basket being fully open. In one embodiment, the target opening amount of the basket is set based on the detected size of the urinary stone.

Figure 6:
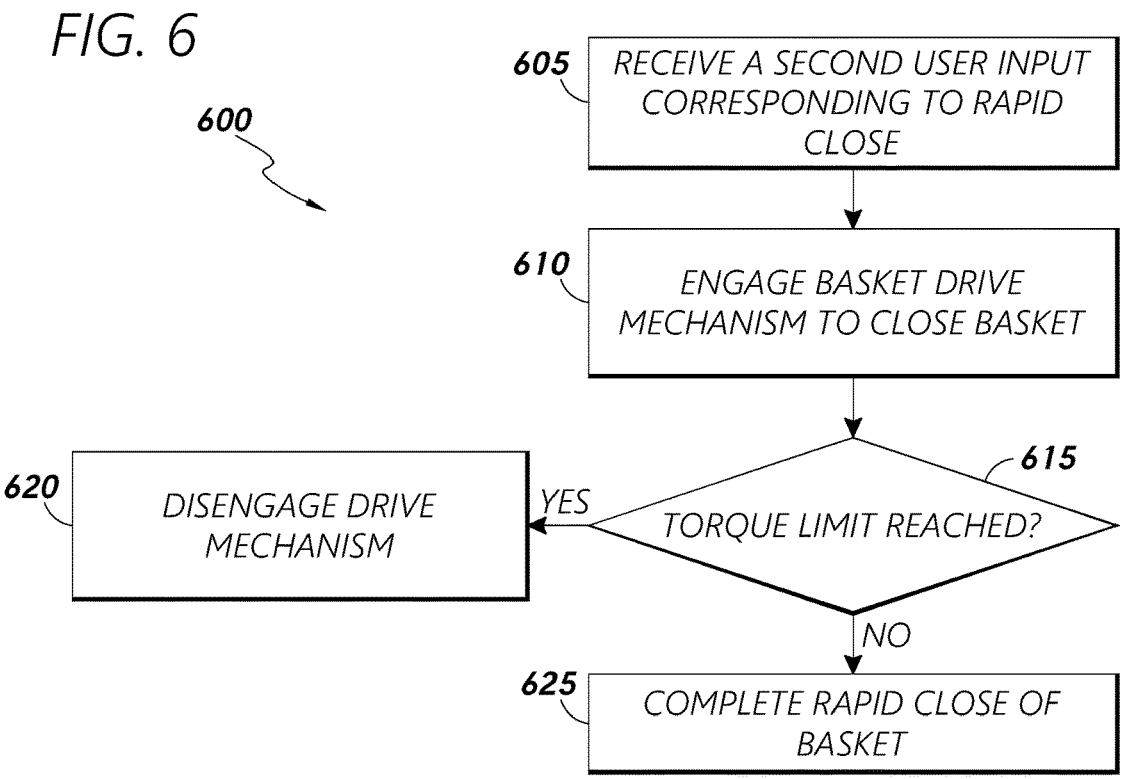
FIG. 6 is a flow diagram of a pre-programed rapid close process, according to certain embodiments.

FIG. 6 is a flow diagram of a pre-programmed rapid close process 600, according to certain embodiments. The rapid close process 600 can be performed by the robotic system 110 or by another component of the medical system 100. For example, the robotic system 110 may be manipulating a basket retrieval device 120 with one or more of its arms. The process 600 may be performed according to the inputs provided by a user (e.g., physician) or may at least be partially automated. While the following describes one possible sequence to the process, other embodiments can perform the process in a different order.

At block 605, the control system 140 of the robotic system 110 receives a second user input from the input device 146. For example, the input may be double-tapping a button, a voice command, or other input. In one embodiment, the second input is double-tapping a second button on the controller 200 of FIGS. 2A-2B.

At block 610, the robotic system 110 engages the basket drive mechanism to close the basket 405 of the basket retrieval device 120 at an accelerated speed. In some embodiments, the basket drive mechanism 420 is configured to operate in at least two speeds: a first speed corresponding to a regular closing speed of the basket, and a second speed faster than the first speed. In one embodiment, the regular closing speed is used when the basket is closed using directly controlled movement rather than a pre-programmed motion.

At block 615, the torque sensor determines the torque being applied by the basket drive mechanism 420 to the basket 405. If the torque meets or exceeds a torque limit configured for the robotic system 110, then the drive mechanism is disengaged. For example, the torque limit may be reached if there is tissue or a urinary stone preventing the basket from closing. If the torque limit is reached, then the process 600 proceeds to block 620. Otherwise, the process 600 proceeds to block 625.

At block 620, the torque limit is reached and the drive mechanism is disengaged. As something is preventing the basket from further closing, additional movement could damage the basket 405 or surrounding tissue.

At block 625, the rapid close movement is completed. The basket 405 may be fully closed (e.g., as indicated by the drive mechanism torque) or have otherwise reached the desired closed configuration. For example, the rapid close movement may be configured to stop at 50%, 60%, 70%, 80%, 90%, 100% or other amount of the basket being fully closed. In one embodiment, the target closed amount of the basket is set based on the detected size of the urinary stone 165. For example, if the urinary stone is large, then the basket may only close a small amount before contacting or surrounding the urinary stone.

Figure 7:
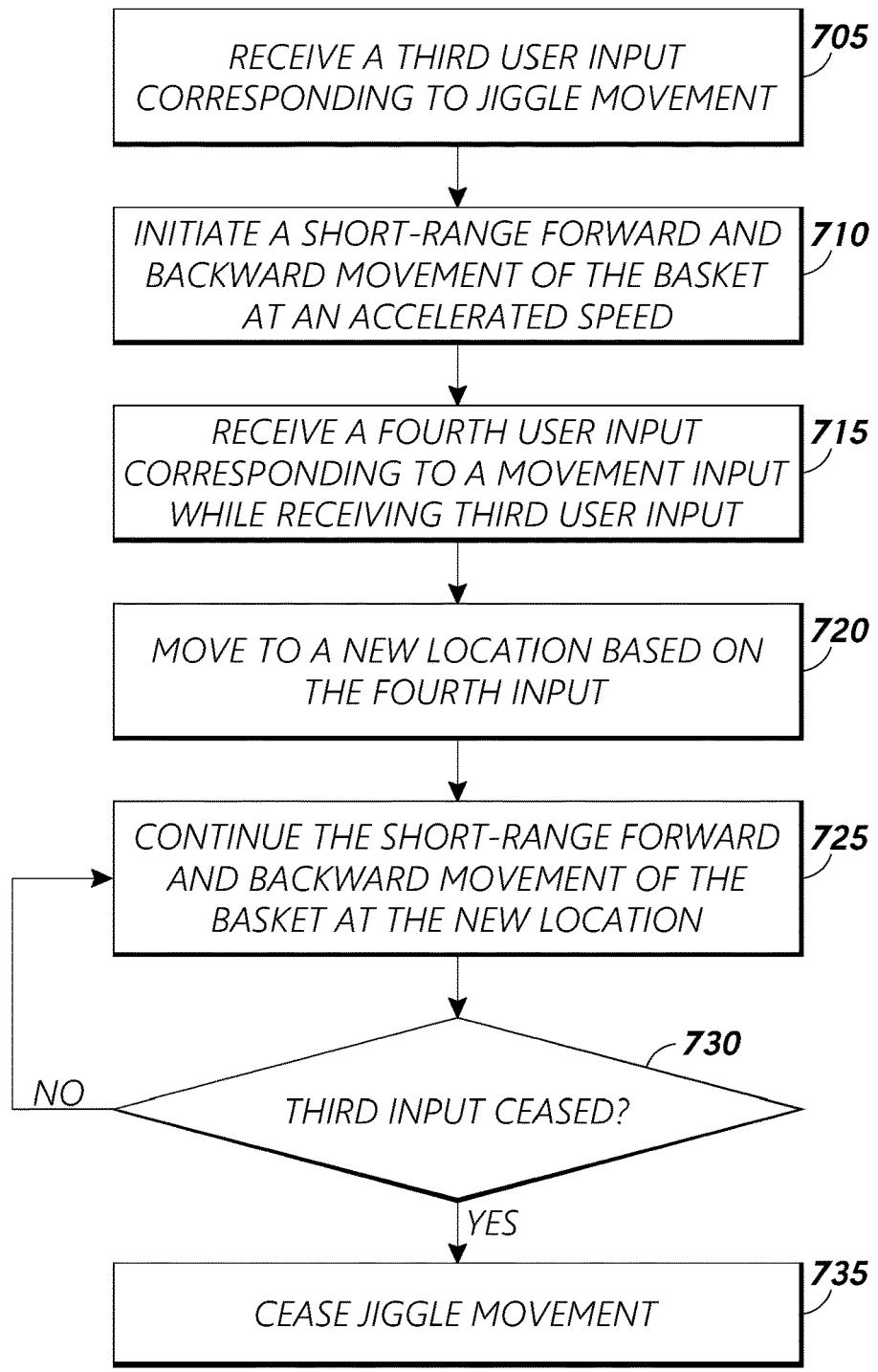
FIG. 7 is a flow diagram of a pre-programed jiggle process, according to certain embodiments.

FIG. 7 is a flow diagram of a pre-programmed jiggle motion process 700, according to certain embodiments. The jiggle process 700 can be performed by the robotic system 110 or by another component of the medical system 100. For example, the robotic system 110 may be manipulating a basket retrieval device 120 with one or more of its arms. The process 700 may be performed according to the inputs provided by a user (e.g., physician) or may at least be partially automated. While the following describes one possible sequence to the process, other embodiments can perform the process in a different order.

At block 705, the control system 140 of the robotic system 110 receives a third user input from the input device 146. For example, the input may be holding down one or more buttons, double-tapping a button, a voice command, or other input. In one embodiment, the third input is holding down the first button (associated with rapid open) and the second button (associated with on rapid close) of controller 200 of FIGS. 2A-2B.

At block 710, the robotic system 110 initiates a short-range forward and backward movement of the basket at an accelerated speed. For example, the basket may move a few millimeters back and forth. In some situations, the basket may move a few centimeters. In some embodiments, the basket drive mechanism 420 is configured to operate the basket in at least two speeds: a first speed corresponding to a regular movement speed of the basket, and a second speed faster than the first speed. In one embodiment, the regular movement speed is used when the basket is moving using directly controlled movement rather than a pre-programmed motion.

At block 715, the control system 140 receives a fourth user input corresponding to a movement input, while receiving the third user input. In one embodiment, the fourth input is movement along an axis (e.g., forward or backward) of a joystick of the controller 200. For example, the physician 160 can move the joystick while holding down the first and second buttons.

At block 720, the robotic system 110 moves the basket to a new location based on the fourth input. For example, if the joystick is moved up, the basket is further inserted into the patient. If the joystick is moved back, the basket is retracted towards the proximal end of the basket retrieval device 120.

At block 725, the robotic system 110 continues the short-range forward and backward movement of the basket at the new location. The locus or center of the movement is the new location.

At block 730, if the third input has ceased (e.g., the physician 160 has released the first button and second button), the process 700 proceeds to block 735 and the jiggle motion ceases. If the third input is still ongoing, the process 700 proceeds to block 725 and the robotic system 110 continues the forward and backward movement of the basket. In other embodiments, the jiggle motion stops in response to other input, after a certain amount of time has passed, or after certain amount of repetitions of movement have completed.

Example Robotic System

Figure 8:
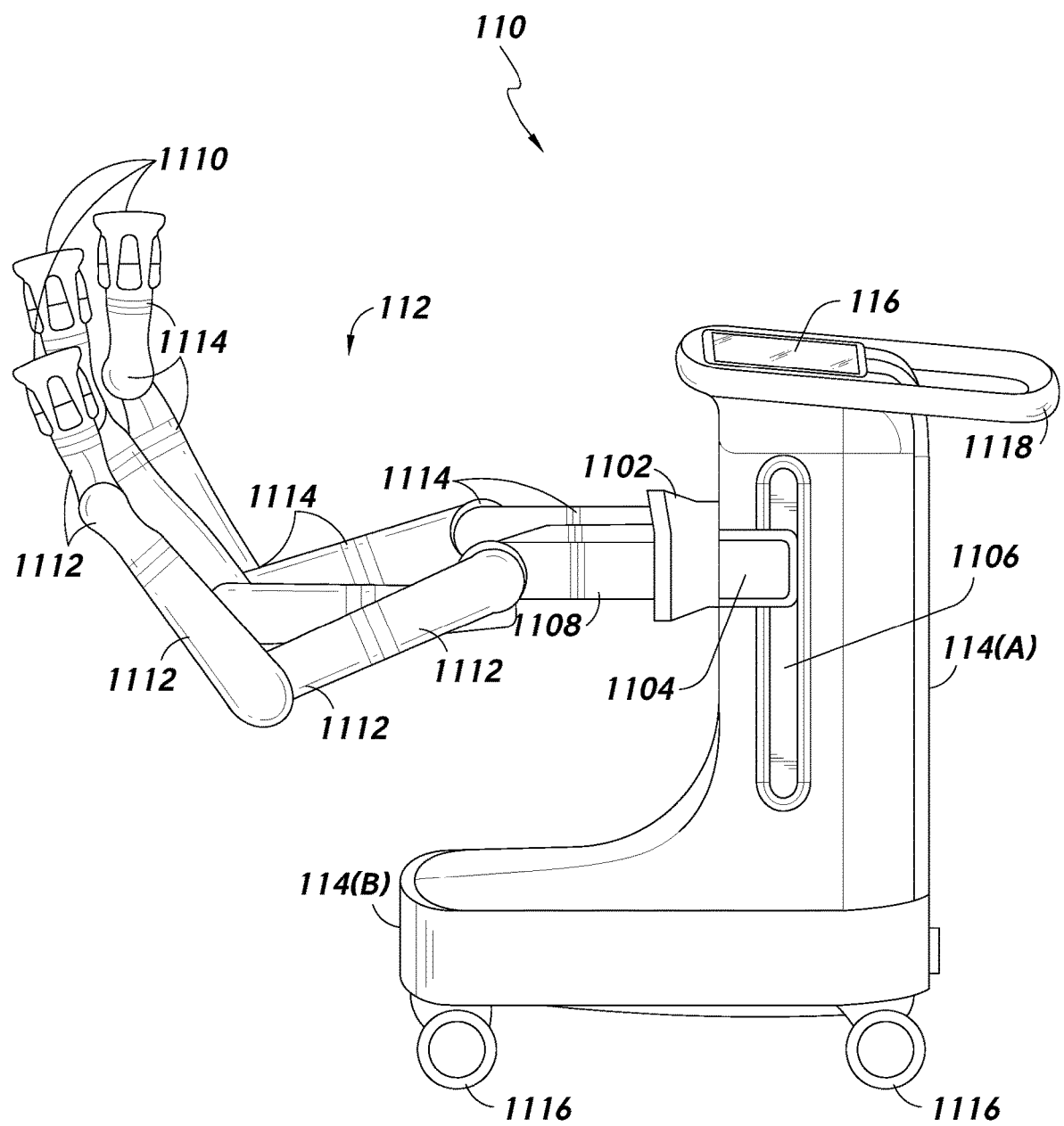
FIG. 8 illustrates example details of the robotic system 110, according to certain embodiments.

FIG. 8 illustrates example details of the robotic system 110 in accordance with one or more embodiments. In this example, the robotic system 110 is illustrated as a cart-based robotically-enabled system that is movable. However, the robotic system 110 can be implemented as a stationary system, integrated into a table, and so on.

The robotic system 110 can include the support structure 114 including an elongated section 114(A) (sometimes referred to as "the column 114(A)") and a base 114(B). The column 114(A) can include one or more carriages, such as a carriage 1102 (alternatively referred to as "the arm support 1102") for supporting the deployment of one or more of the robotic arms 112 (three shown in FIG. 8). The carriage 1102 can include individually configurable arm mounts that rotate along a perpendicular axis to adjust the base of the robotic arms 112 for positioning relative to a patient. The carriage 1102 also includes a carriage interface 1104 that allows the carriage 1102 to vertically translate along the column 114 (A). The carriage interface 1104 is connected to the column 114(A) through slots, such as slot 1106, that are positioned on opposite sides of the column 114(A) to guide the vertical translation of the carriage 1102. The slot 1106 includes a vertical translation interface to position and hold the carriage 1102 at various vertical heights relative to the base 114(B). Vertical translation of the carriage 1102 allows the robotic system 110 to adjust the reach of the robotic arms 112 to meet a variety of table heights, patient sizes, physician preferences, etc. Similarly, the individually configurable arm mounts on the carriage 1102 allow a robotic arm base 1108 of the robotic arms 112 to be angled in a variety of configurations. The column 114(A) can internally comprise mechanisms, such as gears and/or motors, that are designed to use a vertically aligned lead screw to translate the carriage 1102 in a mechanized fashion in response to control signals generated in response to user inputs, such as inputs from the I/O device(s) 116.

In some embodiments, the slot 1106 can be supplemented with a slot cover(s) that is flush and/or parallel to the slot surface to prevent dirt and/or fluid ingress into the internal chambers of the column 114(A) and/or the vertical translation interface as the carriage 1102 vertically translates. The slot covers can be deployed through pairs of spring spools positioned near the vertical top and bottom of the slot 1106. The covers can be coiled within the spools until deployed to extend and retract from their coiled state as the carriage 1102 vertically translates up and down. The spring-loading of the spools can provide force to retract the cover into a spool when the carriage 1102 translates towards the spool, while also maintaining a tight seal when the carriage 1102 translates away from the spool. The covers can be connected to the carriage 1102 using, for example, brackets in the carriage interface 1104 to ensure proper extension and retraction of the covers as the carriage 1102 translates.

The base 114(B) can balance the weight of the column 114(A), the carriage 1102, and/or arms 112 over a surface, such as the floor. Accordingly, the base 114(B) can house heavier components, such as one or more electronics, motors, power supply, etc., as well as components that enable movement and/or immobilize the robotic system 110. For example, the base 114(B) can include rollable wheels 1116 (also referred to as "the casters 1116") that allow for the robotic system 110 to move around the room for a procedure. After reaching an appropriate position, the casters 1116 can be immobilized using wheel locks to hold the robotic system 110 in place during the procedure. As shown, the robotic system 110 also includes a handle 1118 to assist with maneuvering and/or stabilizing the robotic system 110.

The robotic arms 112 can generally comprise robotic arm bases 1108 and end effectors 1110, separated by a series of linkages 1112 that are connected by a series of joints 1114. Each joint 1114 can comprise an independent actuator and each actuator can comprise an independently controllable motor. Each independently controllable joint 1114 represents an independent degree of freedom available to the robotic arm 112. For example, each of the arms 112 can have seven joints, and thus, provide seven degrees of freedom. However, any number of joints can be implemented with any degrees of freedom. In examples, a multitude of joints can result in a multitude of degrees of freedom, allowing for "redundant" degrees of freedom. Redundant degrees of freedom allow the robotic arms 112 to position their respective end effectors 1110 at a specific position, orientation, and/or trajectory in space using different linkage positions and/or joint angles. In some embodiments, the end effectors 1110 can be configured to engage with and/or control a medical instrument, a device, an object, and so on. The freedom of movement of the arms 112 can allow the robotic system 110 to position and/or direct a medical instrument from a desired point in space and/or allow a physician to move the arms 112 into a clinically advantageous position away from the patient to create access, while avoiding arm collisions.

As shown in FIG. 8, the robotic system 110 can also include the I/O device(s) 116. The I/O device(s) 116 can include a display, a touchscreen, a touchpad, a projector, a mouse, a keyboard, a microphone, a speaker, a controller, a camera (e.g., to receive gesture input), or another I/O device to receive input and/or provide output. The I/O device(s) 116 can be configured to receive touch, speech, gesture, or any other type of input. The I/O device(s) 116 can be positioned at the vertical end of column 114(A) (e.g., the top of the column 114(A)) and/or provide a user interface for receiving user input and/or for providing output. For example, the I/O device(s) 116 can include a touchscreen (e.g., a dual-purpose device) to receive input and provide a physician with pre-operative and/or intra-operative data. Example pre-operative data can include pre-operative plans, navigation, and/or mapping data derived from pre-operative computerized tomography (CT) scans, and/or notes from pre-operative patient interviews. Example intra-operative data can include optical information provided from a tool/instrument, sensor, and/or coordinate information from sensors, as well as vital patient statistics, such as respiration, heart rate, and/or pulse. The I/O device(s) 116 can be positioned and/or tilted to allow a physician to access the I/O device(s) 116 from a variety of positions, such as the side of the column 114(A) opposite the carriage 1102. From this position, the physician can view the I/O device(s) 116, the robotic arms 112, and/or a patient while operating the I/O device(s) 116 from behind the robotic system 110.

The robotic system 110 can include a variety of other components. For example, the robotic system 110 can include one or more control electronics/circuitry, power sources, pneumatics, optical sources, actuators (e.g., motors to move the robotic arms 112), memory, and/or communication interfaces (e.g. to communicate with another device). In some embodiments, the memory can store computer-executable instructions that, when executed by the control circuitry, cause the control circuitry to perform any of the operations discussed herein. For example, the memory can store computer-executable instructions that, when executed by the control circuitry, cause the control circuitry to receive input and/or a control signal regarding manipulation of the robotic arms 112 and, in response, control the robotic arms 112 to be positioned in a particular arrangement and/or to navigate a medical instrument connected to the end effectors 1110.

In some embodiments, robotic system 110 is configured to engage with and/or control a medical instrument, such as the basket retrieval device 120. For example, the robotic arms 112 can be configured to control a position, orientation, and/or tip articulation of a scope (e.g., a sheath and/or a leader of the scope). In some embodiments, the robotic arms 112 can be configured/configurable to manipulate the scope using elongate movement members. The elongate movement members can include one or more pull wires (e.g., pull or push wires), cables, fibers, and/or flexible shafts. To illustrate, the robotic arms 112 can be configured to actuate multiple pull wires coupled to the scope to deflect the tip of the scope. Pull wires can include any suitable or desirable materials, such as metallic and/or non-metallic materials such as stainless steel, Kevlar, tungsten, carbon fiber, and the like. In some embodiments, the scope is configured to exhibit nonlinear behavior in response to forces applied by the elongate movement members. The nonlinear behavior can be based on stiffness and compressibility of the scope, as well as variability in slack or stiffness between different elongate movement members.

Example Control System

Figure 9:
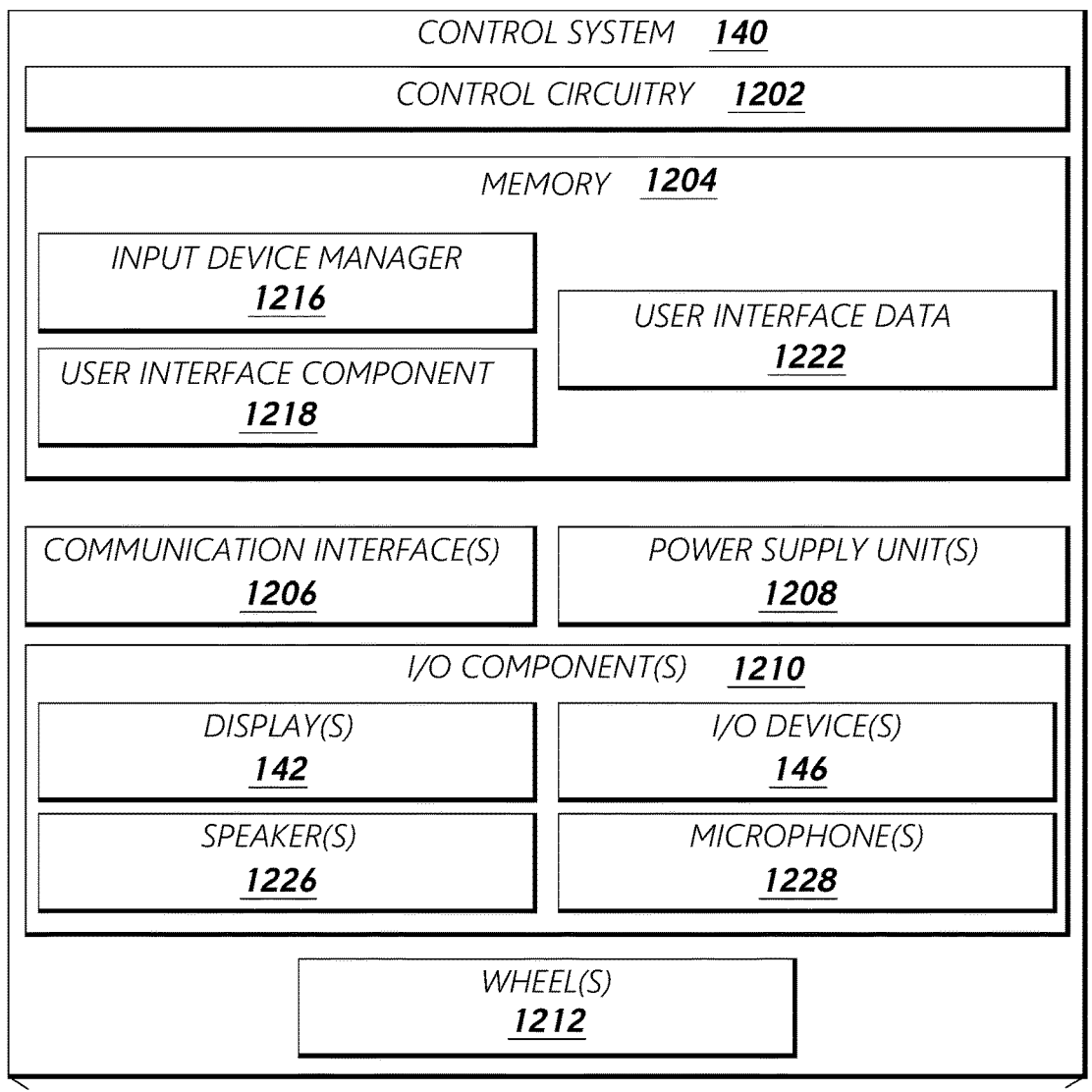
FIG. 9 illustrates example details of the control system 140, according to certain embodiments.
Figure 9:
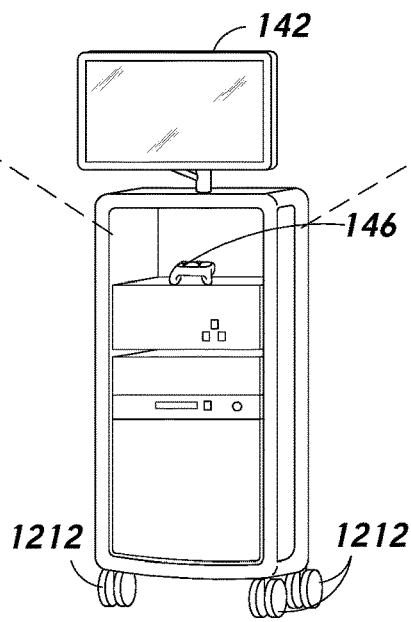

FIG. 9 illustrates example details of the control system 140 in accordance with one or more embodiments. As illustrated, the control system 140 can include one or more of the following components, devices, modules, and/or units (referred to herein as "components"), either separately/individually and/or in combination/collectively: control circuitry 1202, data storage/memory 1204, one or more communication interfaces 1206, one or more power supply units 1208, one or more I/O components 1210, and/or one or more wheels 1212 (e.g., casters or other types of wheels). In some embodiments, the control system 140 can comprise a housing/enclosure configured and/or dimensioned to house or contain at least part of one or more of the components of the control system 140. In this example, the control system 140 is illustrated as a cart-based system that is movable with the one or more wheels 1212. In some cases, after reaching the appropriate position, the one or more wheels 1212 can be immobilized using wheel locks to hold the control system 140 in place. However, the control system 140 can be implemented as a stationary system, integrated into another system/device, and so on.

Although certain components of the control system 140 are illustrated in FIG. 9, it should be understood that additional components not shown can be included in embodiments in accordance with the present disclosure. Furthermore, certain of the illustrated components can be omitted in some embodiments. Although the control circuitry 1202 is illustrated as a separate component in the diagram of FIG. 9, it should be understood that any or all of the remaining components of the control system 140 can be embodied at least in part in the control circuitry 1202. That is, the control circuitry 1202 can include various devices (active and/or passive), semiconductor materials and/or areas, layers, regions, and/or portions thereof, conductors, leads, vias, connections, and/or the like, wherein one or more of the other components of the control system 140 and/or portion(s) thereof can be formed and/or embodied at least in part in/by such circuitry components/devices.

The various components of the control system 140 can be electrically and/or communicatively coupled using certain connectivity circuitry/devices/features, which can or may not be part of the control circuitry 1202. For example, the connectivity feature(s) can include one or more printed circuit boards configured to facilitate mounting and/or interconnectivity of at least some of the various components/circuitry of the control system 140. In some embodiments, two or more of the control circuitry 1202, the data storage/memory 1204, the communication interface(s) 1206, the power supply unit(s) 1208, and/or the input/output (I/O) component(s) 1210, can be electrically and/or communicatively coupled to each other.

As illustrated, the memory 1204 can include an input device manager 1216 and a user interface component 1218 configured to facilitate various functionality discussed herein. In some embodiments, the input device manager 1216, and/or the user interface component 1218 can include one or more instructions that are executable by the control circuitry 1202 to perform one or more operations. Although many embodiments are discussed in the context of the components 1216-1218 including one or more instructions that are executable by the control circuitry 1202, any of the components 1216-1218 can be implemented at least in part as one or more hardware logic components, such as one or more application specific integrated circuits (ASIC), one or more field-programmable gate arrays (FPGAs), one or more program-specific standard products (ASSPs), one or more complex programmable logic devices (CPLDs), and/or the like. Furthermore, although the components 1216-1218 are illustrated as being included within the control system 140, any of the components 1216-1218 can be implemented at least in part within another device/system, such as the robotic system 110, the table 150, or another device/system. Similarly, any of the other components of the control system 140 can be implemented at least in part within another device/system.

The input device manager 1216 can be configured to receive inputs from the input device 146 and translate them into actions performable by the robotic system 110. For example, pre-programmed motions, such as rapid open, rapid close, and jiggle motion, can be stored in the input device manager 1216. These pre-programmed motions can then be assigned to the desired input (e.g., single or dual button presses, voice commands, joystick movements, etc.). In some implementations, the pre-programmed motions are determined by the manufacturer. In other implementations, users may be able to modify existing pre-programmed motions and/or create new ones.

The user interface component 1218 can be configured to facilitate one or more user interfaces (also referred to as "one or more graphical user interfaces (GUI)"). For example, the user interface component 1218 can generate a configuration menu for assigning pre-programmed motions to inputs or a settings menu for enabling certain modes of operation or disabling selected pre-programmed motions in specific situations. The user interface component 1218 can also provide user interface data 1222 for display to the user.

The one or more communication interfaces 1206 can be configured to communicate with one or more device/sensors/systems. For example, the one or more communication interfaces 1206 can send/receive data in a wireless and/or wired manner over a network. A network in accordance with embodiments of the present disclosure can include a local area network (LAN), wide area network (WAN) (e.g., the Internet), personal area network (PAN), body area network (BAN), etc. In some embodiments, the one or more communication interfaces 1206 can implement a wireless technology such as Bluetooth, Wi-Fi, near field communication (NFC), or the like.

The one or more power supply units 1208 can be configured to manage power for the control system 140 (and/or the robotic system 110, in some cases). In some embodiments, the one or more power supply units 1208 include one or more batteries, such as a lithium-based battery, a lead-acid battery, an alkaline battery, and/or another type of battery. That is, the one or more power supply units 1208 can comprise one or more devices and/or circuitry configured to provide a source of power and/or provide power management functionality. Moreover, in some embodiments the one or more power supply units 1208 include a mains power connector that is configured to couple to an alternating current (AC) or direct current (DC) mains power source.

The one or more I/O components 1210 can include a variety of components to receive input and/or provide output, such as to interface with a user. The one or more I/O components 1210 can be configured to receive touch, speech, gesture, or any other type of input. In examples, the one or more I/O components 1210 can be used to provide input regarding control of a device/system, such as to control the robotic system 110, navigate the scope or other medical instrument attached to the robotic system 110, control the table 150, control the fluoroscopy device 190, and so on. As shown, the one or more I/O components 1210 can include the one or more displays 142 (sometimes referred to as "the one or more display devices 142") configured to display data. The one or more displays 142 can include one or more liquid-crystal displays (LCD), light-emitting diode (LED) displays, organic LED displays, plasma displays, electronic paper displays, and/or any other type(s) of technology. In some embodiments, the one or more displays 142 include one or more touchscreens configured to receive input and/or display data. Further, the one or more I/O components 1210 can include the one or more input devices 146, which can include a touchscreen, touch pad, controller, mouse, keyboard, wearable device (e.g., optical head-mounted display), virtual or augmented reality device (e.g., head-mounted display), etc. Additionally, the one or more I/O components 1210 can include one or more speakers 1226 configured to output sounds based on audio signals and/or one or more microphones 1228 configured to receive sounds and generate audio signals. In some embodiments, the one or more I/O components 1210 include or are implemented as a console.

Although not shown in FIG. 9, the control system 140 can include and/or control other components, such as one or more pumps, flow meters, valve controls, and/or fluid access components in order to provide controlled irrigation and/or aspiration capabilities to a medical instrument (e.g., a scope), a device that can be deployed through a medical instrument, and so on. In some embodiments, irrigation and aspiration capabilities can be delivered directly to a medical instrument through separate cable(s). Further, the control system 140 can include a voltage and/or surge protector designed to provide filtered and/or protected electrical power to another device, such as the robotic system 110, thereby avoiding placement of a power transformer and other auxiliary power components in robotic system 110, resulting in a smaller, more moveable robotic system 110.

The control system 140 can also include support equipment for sensors deployed throughout the medical system 100. For example, the control system 140 can include opto-electronics equipment for detecting, receiving, and/or processing data received from optical sensors and/or cameras. Such opto-electronics equipment can be used to generate real-time images for display in any number of devices/systems, including in the control system 140.

In some embodiments, the control system 140 can be coupled to the robotic system 110, the table 150, and/or a medical instrument, such as the scope and/or the basket retrieval device 120, through one or more cables or connections (not shown). In some implementations, support functionality from the control system 140 can be provided through a single cable, simplifying and de-cluttering an operating room. In other implementations, specific functionality can be coupled in separate cabling and connections. For example, while power can be provided through a single power cable, the support for controls, optics, fluidics, and/or navigation can be provided through a separate cable.

The term "control circuitry" is used herein according to its broad and ordinary meaning, and can refer to any collection of one or more processors, processing circuitry, processing modules/units, chips, dies (e.g., semiconductor dies including come or more active and/or passive devices and/or connectivity circuitry), microprocessors, micro-controllers, digital signal processors, microcomputers, central processing units, graphics processing units, field programmable gate arrays, programmable logic devices, state machines (e.g., hardware state machines), logic circuitry, analog circuitry, digital circuitry, and/or any device that manipulates signals (analog and/or digital) based on hard coding of the circuitry and/or operational instructions. Control circuitry can further comprise one or more, storage devices, which can be embodied in a single memory device, a plurality of memory devices, and/or embedded circuitry of a device. Such data storage can comprise read-only memory, random access memory, volatile memory, non-volatile memory, static memory, dynamic memory, flash memory, cache memory, data storage registers, and/or any device that stores digital information. It should be noted that in embodiments in which control circuitry comprises a hardware state machine (and/or implements a software state machine), analog circuitry, digital circuitry, and/or logic circuitry, data storage device(s)/register(s) storing any associated operational instructions can be embedded within, or external to, the circuitry comprising the state machine, analog circuitry, digital circuitry, and/or logic circuitry.

The term "memory" is used herein according to its broad and ordinary meaning and can refer to any suitable or desirable type of computer-readable media. For example, computer-readable media can include one or more volatile data storage devices, non-volatile data storage devices, removable data storage devices, and/or nonremovable data storage devices implemented using any technology, layout, and/or data structure(s)/protocol, including any suitable or desirable computer-readable instructions, data structures, program modules, or other types of data.

Computer-readable media that can be implemented in accordance with embodiments of the present disclosure includes, but is not limited to, phase change memory, static random-access memory (SRAM), dynamic random-access memory (DRAM), other types of random access memory (RAM), read-only memory (ROM), electrically erasable programmable read-only memory (EEPROM), flash memory or other memory technology, compact disk read-only memory (CD-ROM), digital versatile disks (DVD) or other optical storage, magnetic cassettes, magnetic tape, magnetic disk storage or other magnetic storage devices, or any other non-transitory medium that can be used to store information for access by a computing device. As used in certain contexts herein, computer-readable media may not generally include communication media, such as modulated data signals and carrier waves. As such, computer-readable media should generally be understood to refer to non-transitory media.

Additional Embodiments

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y, and Z," unless specifically stated otherwise, is understood with the context as used in general to convey that an item, term, element, etc. may be either X, Y, or Z. Thus, such conjunctive language is not generally intended to imply that certain embodiments require at least one of X, at least one of Y, and at least one of Z to each be present.

It should be appreciated that in the above description of embodiments, various features are sometimes grouped together in a single embodiment, Figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

It should be understood that certain ordinal terms (e.g., "first" or "second") may be provided for ease of reference and do not necessarily imply physical characteristics or ordering. Therefore, as used herein, an ordinal term (e.g., "first," "second," "third," etc.) used to modify an element, such as a structure, a component, an operation, etc., does not necessarily indicate priority or order of the element with respect to any other element, but rather may generally distinguish the element from another element having a similar or identical name (but for use of the ordinal term). In addition, as used herein, indefinite articles ("a" and "an") may indicate "one or more" rather than "one." Further, an operation performed "based on" a condition or event may also be performed based on one or more other conditions or events not explicitly recited.

Unless otherwise defined, all terms (including technical and scientific terms) used herein have the same meaning as commonly understood by one of ordinary skill in the art to which example embodiments belong. It be further understood that terms, such as those defined in commonly used dictionaries, should be interpreted as having a meaning that is consistent with their meaning in the context of the relevant art and not be interpreted in an idealized or overly formal sense unless expressly so defined herein.

Unless otherwise expressly stated, comparative and/or quantitative terms, such as "less," "more," "greater," and the like, are intended to encompass the concepts of equality. For example, "less" can mean not only "less" in the strictest mathematical sense, but also, "less than or equal to."

What is claimed is:

1. A robotic system for performing a medical procedure, the robotic system comprising:
   a robotic manipulator configured to:
      manipulate a medical instrument comprising a basket, the medical instrument configured to access a human anatomy;
      open the basket at a first opening speed and a second opening speed faster than the first opening speed; and
      close the basket at a first closing speed and a second closing speed faster than the first closing speed;
   an input device configured to receive one or more user interactions and initiate one or more actions by the robotic manipulator, the one or more actions comprising at least one of directly controlled movement and pre-programmed motions; and
   control circuitry communicatively coupled to the input device and the robotic manipulator and configured to:
      in response to receiving a first user interaction via the input device, trigger a first pre-programmed motion of the robotic manipulator, the first pre-programmed motion comprising opening the basket at the second opening speed; and
      in response to receiving a second user interaction via the input device, trigger a second pre-programmed motion of the robotic manipulator, the second pre-programmed motion comprising closing the basket at the second closing speed.

2. The robotic system of claim 1, wherein the medical instrument further comprises a ureteroscope.

3. The robotic system of claim 1, wherein the medical procedure comprises ureteroscopy.

4. The robotic system of claim 1, wherein the input device comprises a control pad, the control pad comprising:
   directional controls configured to direct movement of the robotic manipulator along a plurality of axes; and
   a plurality of buttons including a first button and a second button.

5. The robotic system of claim 4, wherein the first user interaction comprises double tapping the first button.

6. The robotic system of claim 5, wherein the second user interaction comprises double tapping the second button.

7. The robotic system of claim 6, the control circuitry further configured to:
   in response to tapping the first button and the second button concurrently, trigger a third pre-programmed motion of the robotic manipulator comprising a repeated, short range, forward and backward movement at an accelerated speed.

8. The robotic system of claim 1, the control circuitry further configured to:
   in response to receiving a third user interaction, trigger a third pre-programmed motion of the robotic manipulator comprising a repeated, short range, forward and backward movement at an accelerated speed.

9. The robotic system of claim 1, wherein the second pre-programmed motion further comprises:
   detecting a torque on a drive mechanism of the basket; and
   in response to the torque exceeding a threshold, stopping the closing of the basket.

10. The robotic system of claim 1, wherein the at least one of the first user interaction and the second user interaction comprises a voice command.

11. A method for controlling a medical instrument using a robotic manipulator, the method comprising:
   manipulating, using the robotic manipulator, a medical instrument comprising a basket to access a human anatomy, the robotic manipulator configured to open the basket at a first opening speed and a second opening speed, the robotic manipulator further configured to close the basket at a first closing speed and a second closing speed;
   receiving, via an input device, one or more user interactions for triggering pre-programmed actions by the robotic manipulator;
   in response to receiving a first user interaction via the input device, triggering a first pre-programmed motion of the robotic manipulator, the first pre-programmed motion comprising opening the basket at the second opening speed, the second opening speed faster than the first opening speed; and
   in response to receiving a second user interaction via the input device, triggering a second pre-programmed motion of the robotic manipulator, the second pre-programmed motion comprising closing the basket at the second closing speed, the second closing speed faster than the first closing speed.

12. The method of claim 11, wherein the first user interaction comprises double tapping a first button of the input device and second user interaction comprises double tapping a second button of the input device.

13. The method of claim 12, the method comprising:
   in response to tapping the first button and the second button concurrently, triggering a third pre-programmed motion of the robotic manipulator, the third pre-programmed motion comprising a repeated, short range, forward and backward movement at an accelerated speed.

14. The method of claim 13, the method comprising:
   in response to receiving a movement input along a first axis on the input device, moving a central locus of the third pre-programmed motion of the robotic manipulator along the first axis; and
   repeating the short range, forward and backward movement at the central locus.

15. The method of claim 13, wherein the third pre-programmed motion further comprises a repeated, rotational movement.

16. The method of claim 11, the method comprising:
   manipulating, using the robotic manipulator, an endoscope to access a human anatomy, the endoscope configured to capture images of the medical instrument within the human anatomy.

17. The method of claim 11, the method comprising:
   receiving, via an input device, a third user interaction for directly controlling movement of the medical instrument; and
   manipulating, using the robotic manipulator, the medical instrument along one or more axes of movement based on the received third user interaction.

18. The method of claim 11, wherein the second pre-programmed motion further comprises:
   detecting a torque on a drive mechanism of the basket; and
   in response to the torque exceeding a threshold, stopping the closing of the basket.

19. A control system for controlling a robotic device for performing a medical procedure, the control system comprising:

an input device configured to receive one or more user interactions and initiate one or more actions by the robotic device, the one or more actions comprising at least one of directly-controlled movement and pre-programmed motions;

a communication interface configured to send commands to the robotic device corresponding to the directly-controlled movement and the pre-programmed motions, the commands comprising:
- movement, by the robotic device, of a medical instrument comprising a basket, the medical instrument configured to access a human anatomy;
- opening the basket at a first opening speed and a second opening speed faster than the first opening speed; and
- closing the basket at a first closing speed and a second closing speed faster than the first closing speed; and control circuitry communicatively coupled to the input device and the communication interface, the control circuitry configured to:
- in response to receiving a first user interaction, trigger a first pre-programmed motion of the robotic device, the first pre-programmed motion comprising opening the basket at the second opening speed; and
- in response to receiving a second user interaction, trigger a second pre-programmed motion of the robotic device, the second pre-programmed motion comprising closing the basket at the second closing speed.

20. The control system of claim 19, wherein the input device comprises:
- directional controls configured to direct movement of the robotic device along a plurality of axes; and
- a plurality of buttons including a first button configured to trigger the first pre-programmed motion and a second button configured to trigger the second pre-programmed motion.

21. The control system of claim 20, wherein:
- double-tapping the first button triggers the first pre-programmed motion; and
- double-tapping the second button triggers the second pre-programmed motion.

22. The control system of claim 20, wherein:
- single tapping the first button triggers a third pre-programmed motion different from the first pre-programmed motion; and
- single-tapping the second button triggers a fourth pre-programmed motion different from the second pre-programmed motion.

23. The control system of claim 20, the control circuitry further configured to:
- in response to tapping the first button and the second button concurrently, trigger a third pre-programmed motion of the robotic device, the third pre-programmed motion comprising a repeated, short range, forward and backward movement at an accelerated speed.

24. The control system of claim 23, the control circuitry further configured to:
- in response to receiving, via the directional controls, a movement request along a first axis, move a central locus of the third pre-programmed motion of the robotic device along the first axis; and
- repeat the short range, forward and backward movement at the central locus.

25. The control system of claim 19, wherein:
- the input device comprises a microphone configured to capture vocal user commands; and
- the control circuitry is further configured to identify a first vocal user command corresponding to the first user interaction, and a second vocal user command corresponding to the second user interaction.

26. The control system of claim 19, wherein:
- the robotic device is located at a first geographic location different from a second geographic location of the control system; and
- the communication interface is further configured to send the commands over a wide area network.

27. One or more non-transitory computer-readable media storing computer-executable instructions that, when executed by control circuitry, cause the control circuitry to perform operations comprising:
- manipulating, using a robotic device, a medical instrument comprising a basket to access a human anatomy, the robotic device configured to open the basket at a first opening speed and a second opening speed, the robotic device further configured to close the basket at a first closing speed and a second closing speed;
- receiving, via an input device, one or more inputs for triggering pre-programmed actions by the robotic device;
- in response to receiving a first input via the input device, triggering a first pre-programmed motion of the robotic device, the first pre-programmed motion comprising opening the basket at the second opening speed, the second opening speed faster than the first opening speed; and
- in response to receiving a second input via the input device, triggering a second pre-programmed motion of the robotic device, the second pre-programmed motion comprising closing the basket at the second closing speed, the second closing speed faster than the first closing speed.

28. The one or more non-transitory computer-readable media of claim 27, wherein the first input comprises double tapping a first button of the input device and second input comprises double tapping a second button of the input device.

29. The one or more non-transitory computer-readable media of claim 28, the computer-executable instructions further configured to cause the control circuitry to perform operations comprising:
- in response to tapping the first button and the second button concurrently, triggering a third pre-programmed motion of the robotic device, the third pre-programmed motion comprising a repeated, short range, forward and backward movement at an accelerated speed.

30. The one or more non-transitory computer-readable media of claim 27, the computer-executable instructions further configured to cause the control circuitry to perform operations comprising:
- receiving, via the input device, a third input for controlling direct movement of the robotic device; and
- manipulating, using the robotic device, the medical instrument along one or more axes of movement based on the received third input.

\* \* \* \* \*